United States Patent
Huang

(10) Patent No.: US 10,988,429 B2
(45) Date of Patent: Apr. 27, 2021

(54) QUINOCHALCONE COMPOUND AND USES THEREOF FOR TREATING CANCER OR INFLAMMATION

(71) Applicant: CHON THERAPEUTICS INC., LTD., Beijing (CN)

(72) Inventor: Bo Huang, Beijing (CN)

(73) Assignee: LIFE-GARDEN BIOTECH, Beijing (CN)

( * ) Notice: Subject to any disclaimer, the term of this patent is extended or adjusted under 35 U.S.C. 154(b) by 0 days.

(21) Appl. No.: 16/897,733

(22) Filed: Jun. 10, 2020

(65) Prior Publication Data

US 2020/0377439 A1 Dec. 3, 2020

Related U.S. Application Data

(63) Continuation of application No. PCT/CN2018/075163, filed on Feb. 2, 2018.

(30) Foreign Application Priority Data

Dec. 11, 2017 (CN) .......................... 201711309136.0

(51) Int. Cl.
*C07C 50/30* (2006.01)
*C07C 50/06* (2006.01)

(52) U.S. Cl.
CPC .............. *C07C 50/30* (2013.01); *C07C 50/06* (2013.01)

(58) Field of Classification Search
CPC .................................. C07C 50/06; C07C 50/30
See application file for complete search history.

(56) References Cited

FOREIGN PATENT DOCUMENTS

| CN | 105085218 A | 11/2015 |
|---|---|---|
| CN | 105085219 A | 11/2015 |
| WO | WO2013054998 A1 | 4/2013 |

OTHER PUBLICATIONS

International Search Report for PCT/CN2018/075163.
D1: "A novel chalcone derivative, LQFM064, induces breast cancer cells death via p53, p21, KIT and PDGFRA", European Journal of Pharmaceutical Sciences, vol. 107, Sep. 30, 2017, pp. 1-15.
D2: "Synthetic chalcones as potential anti-inflammatory and cancer chemopreventive agents", European Journal of Medicinal Chemistry, vol. 40, Issue 1, Jan. 2005, pp. 103-112.
The first Office Action of the priority CN application No. 201711309136.0 (2020).
D1: "Antitumor agents 283. Further elaboration of Desmosdumotin C analogs as potent antitumor agents Activation of spindle assembly checkpoint as possible mode of action", Bioorg. Med. Chem. 19(2011) 1816-1822
D2: "Antitumor agents 259. Design, syntheses, and structure-activity relationship study of desmosdumotin C analogs", J Med Chem. Jul. 12, 2007; 50(14): 3354-3358
D3: "Synthesis, QSAR Study and Antitumor Activity of Desmosdumotin-C Analogues", Chin pharm J., Aug. 2017, vol. 52, No. 16, pp. 1387-1392.
D4: "Clinical Medication Guide and Evaluation", Aug. 31, 2016.

*Primary Examiner* — Joseph R Kosack
(74) *Attorney, Agent, or Firm* — J.C. Patents

(57) ABSTRACT

Presented herein is a quinochalcone compound that displays strong anti-cancer properties and provides for synergistic anti-cancer activity when used in combination with interferon β (IFN-β) or interferon γ (IFN-γ). Accordingly, compositions comprising a quinochalcone compound, or a quinochalcone compound and an interferon are disclosed herein for use in treating cancer. Also presented herein, in some embodiments, are methods of using a quinochalcone compound, and compositions thereof, to treat inflammation.

19 Claims, 15 Drawing Sheets

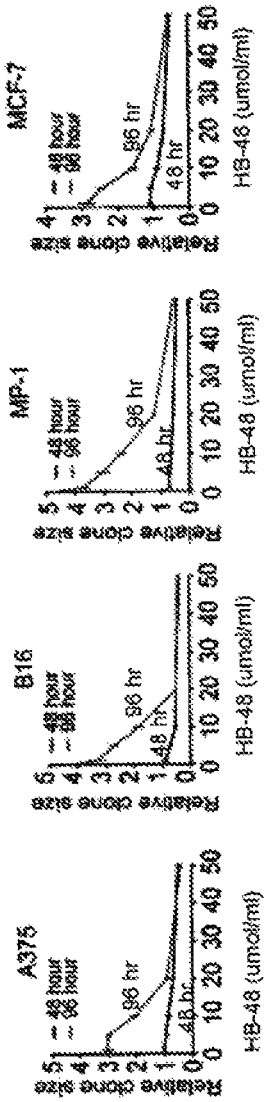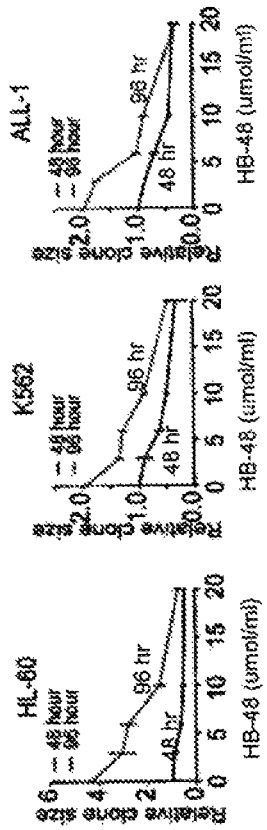

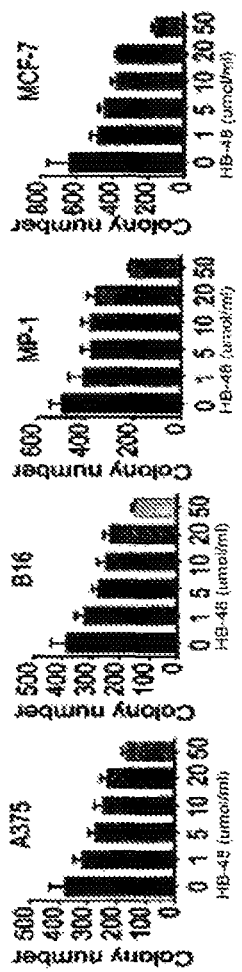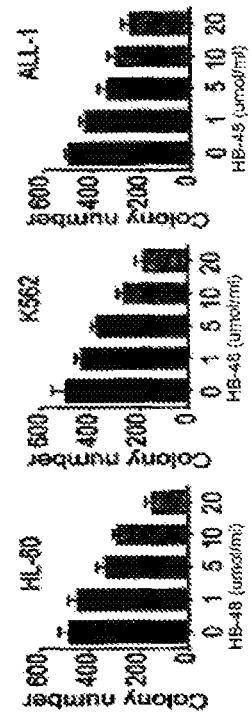

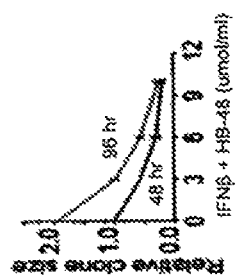
FIG. 4E
FIG. 4F
FIG. 4G

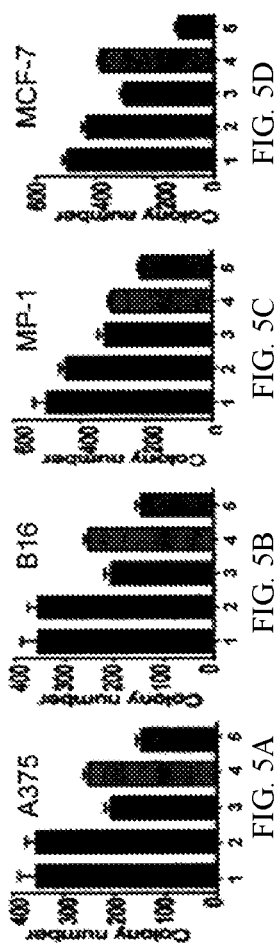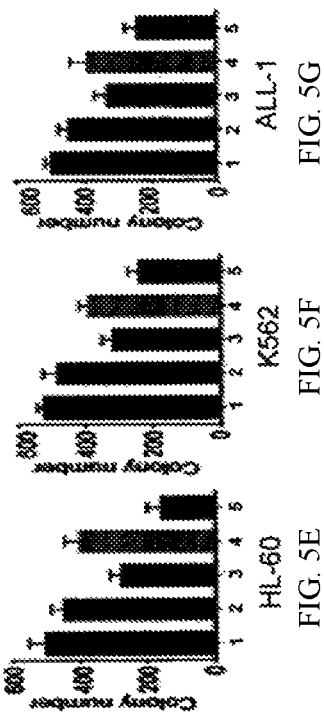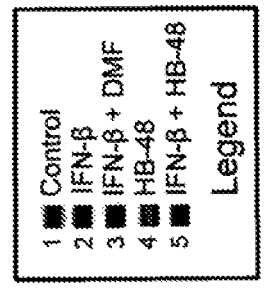
FIG. 5A FIG. 5B FIG. 5C FIG. 5D FIG. 5E FIG. 5F FIG. 5G

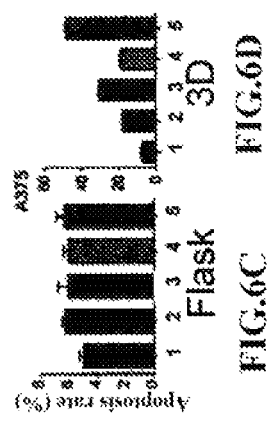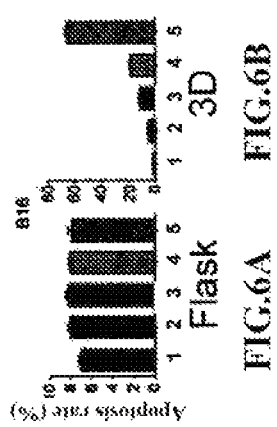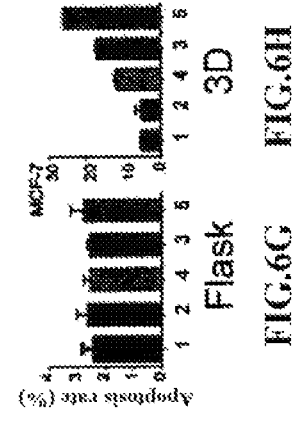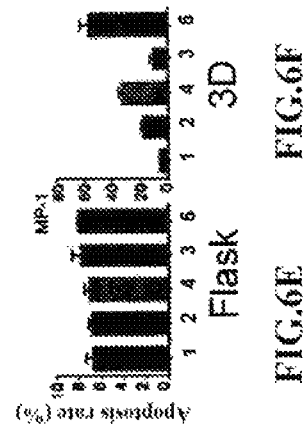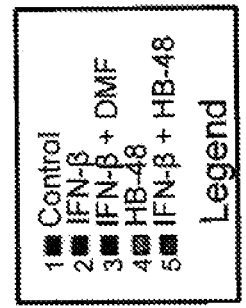

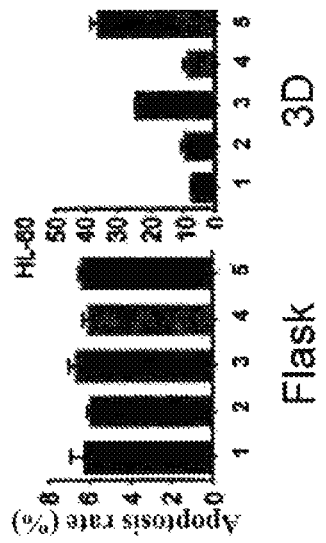
FIG.6I  FIG.6J
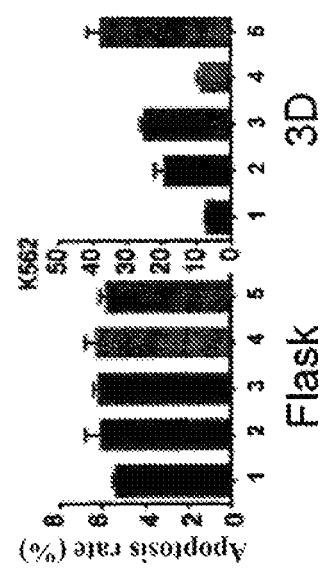
FIG.6K  FIG.6L
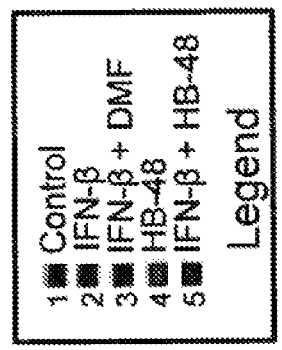
FIG.6M  FIG.6N

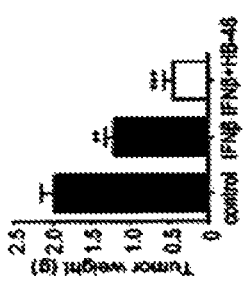
FIG. 7F
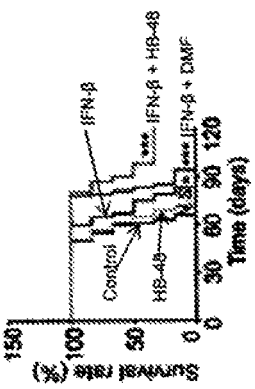
FIG. 7H
FIG. 7E
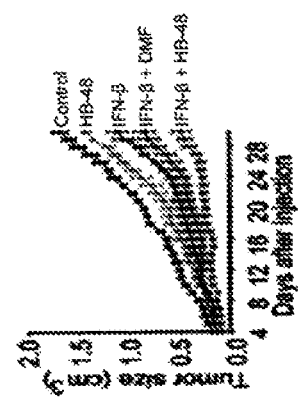
FIG. 7G

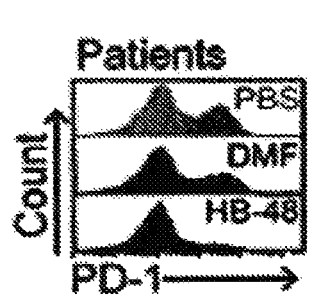 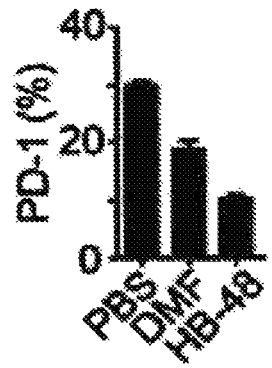
FIG.10A  FIG.10B
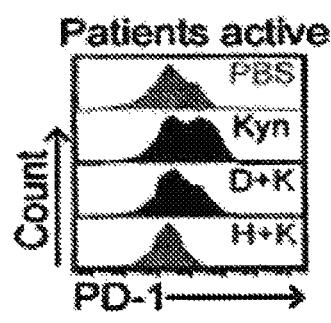 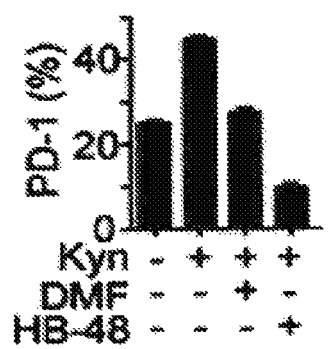
FIG.10C  FIG.10D
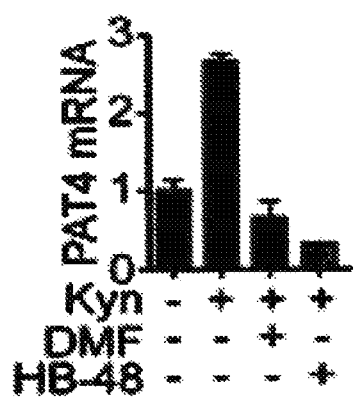
FIG.10E

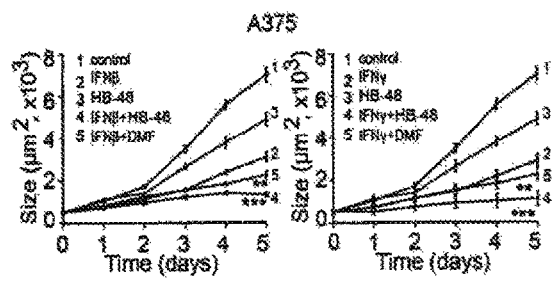
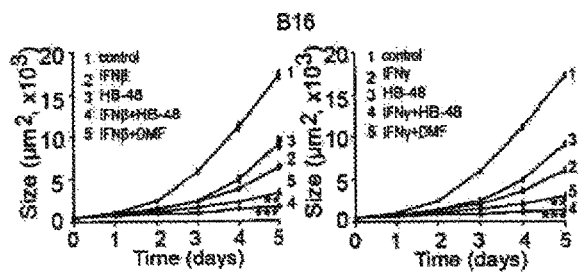
FIG.11A  FIG.11B  FIG.11C  FIG.11D
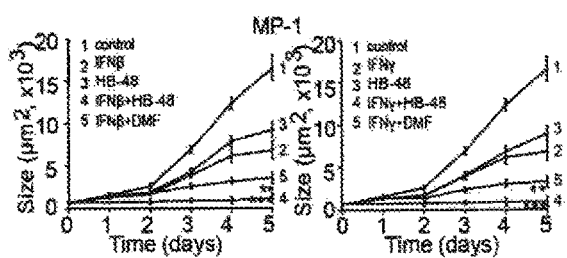
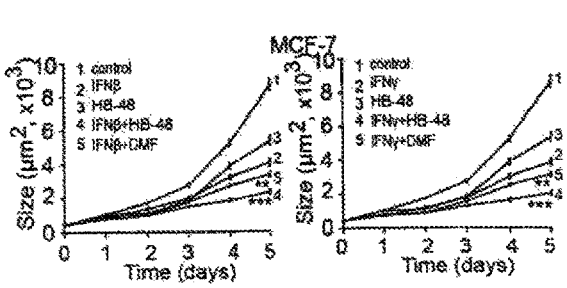
FIG.11E  FIG.11F  FIG.11G  FIG.11H
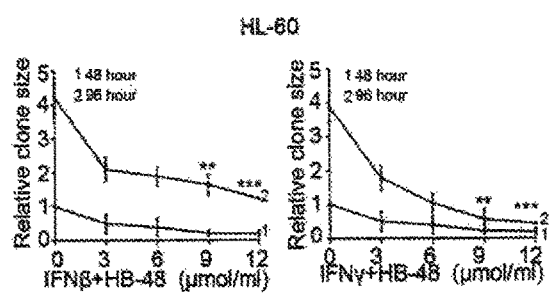
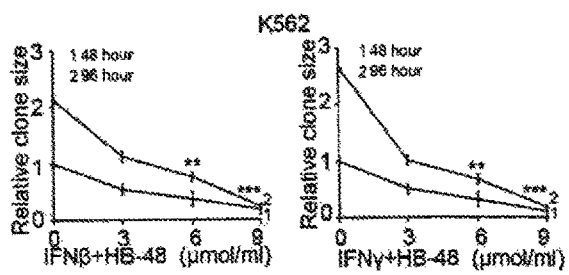
FIG.11I  FIG.11J  FIG.11K  FIG.11L
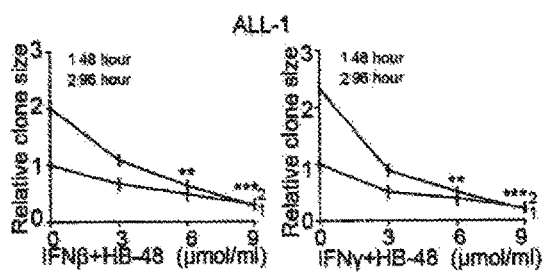
FIG.11M  FIG.11N

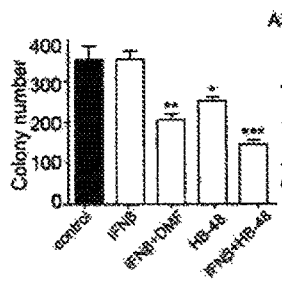 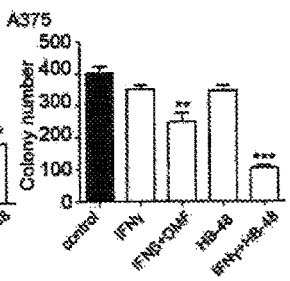 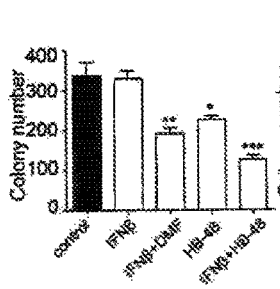 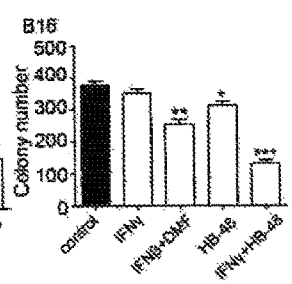
FIG.12A  FIG.12B  FIG.12C  FIG.12D
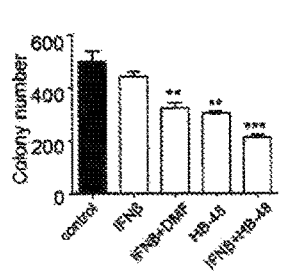 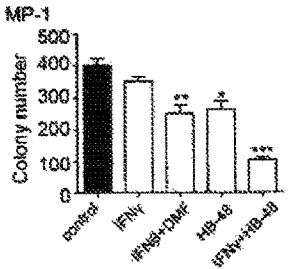 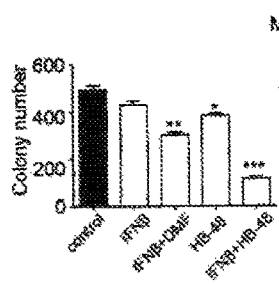 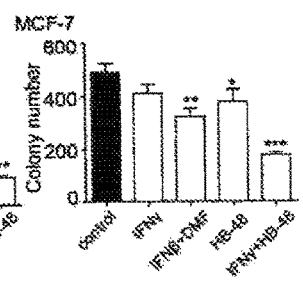
FIG.12E  FIG.12F  FIG.12G  FIG.12H
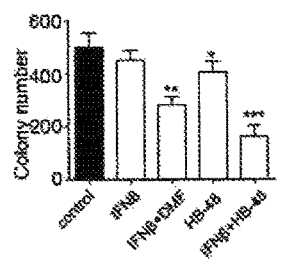 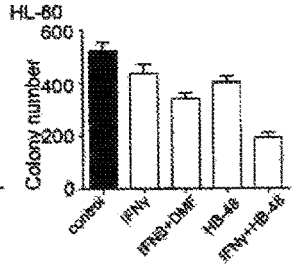 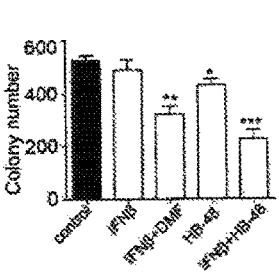 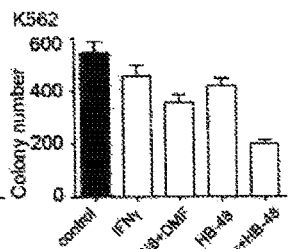
FIG.12I  FIG.12J  FIG.12K  FIG.12L
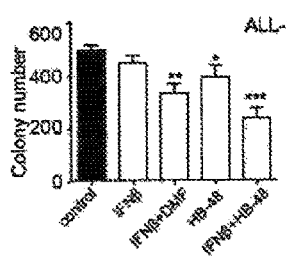 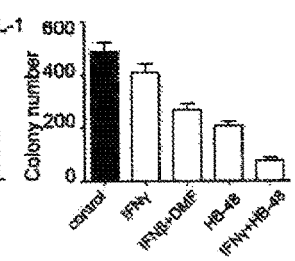
FIG.12M  FIG.12N

QUINOCHALCONE COMPOUND AND USES THEREOF FOR TREATING CANCER OR INFLAMMATION

CROSS-REFERENCE TO RELATED APPLICATIONS

This application is a continuation of International Application No. PCT/CN2018/075163, filed on Feb. 2, 2018, which claims the priority benefit of China Patent Application No. 201711309136.0, filed on Dec. 11, 2017. The contents of the above identified applications are incorporated herein by reference in their entireties.

TECHNICAL FIELD

Embodiments relate to a novel quinochalcone compound, compositions thereof and uses thereof for treating cancer and/or inflammation. Also, certain embodiments relate to the use of a quinochalcone compound to treat cancer, alone or in combination with an interferon (e.g., IFNβ or IFNγ), for treating cancer and/or inflammation. In certain embodiments, a quinochalcone compound and/or an interferon are used in combination with other anti-cancer therapies or other anti-inflammatory agents.

BACKGROUND

Malignancy is a disease caused by the abnormal proliferation of cells. Cancer stem cells play an important role in the survival, proliferation, metastasis and recurrence of tumors. Essentially, cancer stem cells maintain the viability of the tumor cell population through self-renewal and proliferation, and their motility and migratory ability confers the ability to metastasize. In recent years, studies have shown that cancer stem cells can be dormant for a long time and up-regulate the expression of multiple drug-resistant molecules in the course of clinical treatment, but are not sensitive to external physical and chemical factors that kill tumor cells. Tumor cell dormancy is one of the biological characteristics of malignant tumor cells, which is one of the important reason that leads to recurrent and distant invasion and metastasis by tumor cells. Traditional surgery, radiotherapy and chemotherapy have certain clinical effects, accompanied by more serious clinical side effects, and there is a risk of inducing tumor dormancy. Looking for effective and less toxic side effects of treatment to improve patient quality of life has become the focus of medical research.

In vitro use of killer T cells can kill cancer cells, in theory, and the greater the number of killer T cells, the more significant the killing effect. However, the inventors of the present disclosure, in the case of melanoma B16-OVA cells for example, found that even increasing the number of T cells cannot completely eliminate all of the B16-OVA cancer cells. This phenomenon suggests that there is a group of dormant cells that cannot be killed by specific T cells during the clinical treatment of cancer. Dormant cancer cells present a hidden danger for tumor patients because failure of a clinical treatment to completely eliminate all of the dormant cancer cells leaves a patient at risk of tumor recurrence and/or metastasis, which may eventually lead to a patient's death.

Presented herein are compounds, compositions and methods that can effectively kill cancer cells, including dormant tumor cells. Compounds, compositions and methods are also presented herein to treat inflammation.

SUMMARY

In some aspects, presented herein is a method of treating a cancer in a subject in need thereof comprising administering to the subject a therapeutically effective amount of a quinochalcone compound, or a salt thereof, wherein the quinochalcone compound comprises the structure of formula I:

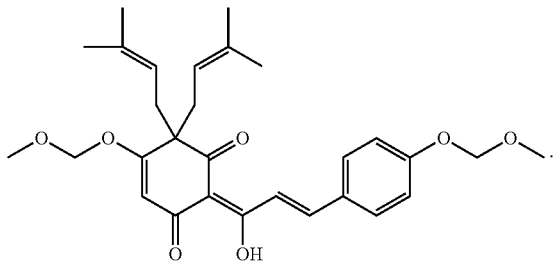

(I)

In some embodiments, the method further comprises administering to the subject a therapeutically effective amount of an interferon, or a variant thereof.

In some aspects, presented herein is a composition comprising a quinochalcone compound, or a salt thereof, wherein the quinochalcone compound comprises the structure of formula I:

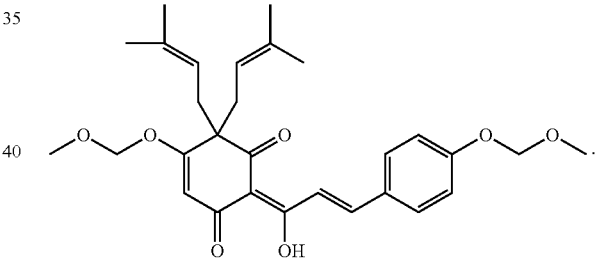

(I)

In some embodiments, the composition further comprising an interferon, or a variant thereof. In certain embodiment, a composition is a pharmaceutical composition comprising one or more pharmaceutically acceptable additives or excipients.

In some embodiments, an interferon is IFN-β or IFN-γ, or a biologically active variant thereof. An interferon can be a human interferon. In some embodiments, a subject is a human subject. In some embodiments, a cancer is selected from a lymphoma, leukemia, hematopoietic neoplasia, myeloma, melanoma and solid tumor. A method of treating a cancer in a subject may further comprising administering an anti-cancer treatment to the subject, for example an anti-cancer vaccine or chemotherapeutic agent. A quinochalcone compound, or a salt thereof, and an interferon (e.g., IFN-β or IFN-γ) can be administered to a subject at the same time or at different times.

In some aspects, presented herein is a method of treating inflammation or an inflammatory condition in a subject in need thereof comprising administering to the subject a therapeutically effective amount of a quinochalcone compound, or a salt thereof, wherein the quinochalcone compound comprises the structure of formula I:

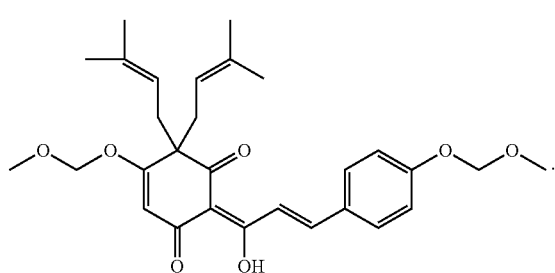

(I)

The method of treating inflammation or an inflammatory condition may further comprising administering an anti-inflammatory agent to the subject. In some embodiments, the inflammation or inflammatory condition comprises an autoimmune disorder or pro-inflammatory condition selected from the group consisting of polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatic, Spondyloarthritides, Pulmonary arterial hypertension, graft-versus-host disease, autoimmune myocarditis, contact hypersensitivity (contact dermatitis), gastro-esophageal reflux disease, erythroderma, Behcet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility, immune-mediated infertility, headache, migraine, pain and swelling.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1(A-G).—Detection of the effect of the quinochalcone compound HB-48 on the size of solid tumor and leukemia cell clones in 3D culture condition. FIGS. 1A through 1G show the relative clone size (y-axis) of the indicated tumor clones after treatment with the indicated concentrations of HB-48 (x-axis) for 48 hours or 96 hours of treatment. All cells were grown in 3D culture conditions. FIG. 1A shows the size of A375 clones of human malignant melanoma. FIG. 1B shows the size of B16 clones of murine melanoma cells. FIG. 1C shows the size of the human malignant melanoma cell line MP-1 obtained from resected tissues of patients with clinical malignant melanoma. FIG. 1D shows the clonal size of MCF-7 human breast cancer cells. FIG. 1E shows the size of HL-60 clones of human leukemia cells. FIG. 1F shows the size of K562 clones of human leukemia cells. FIG. 1G shows the size of human leukemia cells ALL-1.

FIG. 2(A-G)—Detection of the effect of the quinochalcone compound HB-48 on the number of solid tumor and leukemic cell clones in 3D culture conditions. FIGS. 2A through 2G show the number of colonies (y-axis) of the indicated tumor cells after treatment with the indicated concentrations of HB-48 (x-axis). All cells were grown in 3D culture conditions. FIG. 2A shows the number of colonies of human malignant melanoma cells A375. FIG. 2B shows the number of colonies of B16 murine melanoma cells. FIG. 2C shows the number of colonies of human melanoma cells MP-1. FIG. 2D shows the number of colonies of human breast cancer cells MCF-7. FIG. 2E shows the number of colonies of HL-60 colonies of human leukemia cells treated. FIG. 2F shows the number of colonies of K562 human leukemia cells. FIG. 2G shows the number of colonies of human leukemic cells ALL-1.

FIG. 3 shows the effect of HB-48 treatment on B16 tumor volume (y-axis) in C57 mice over time (days, x-axis). C57 mice bearing B16 tumors where treated with 3',4'-Dimethoxyflavone (DMF, vehicle control) or HB-48.

Figure 3:
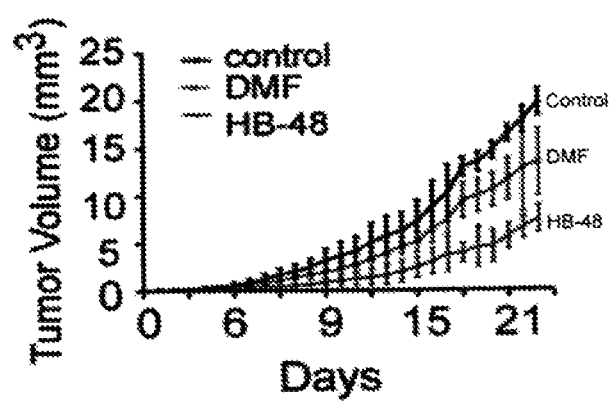
FIG. 3—Evaluation of the inhibitory effect of the quinochalcone compound HB-48 on the growth of solid tumors in vivo.
Figure 4A:
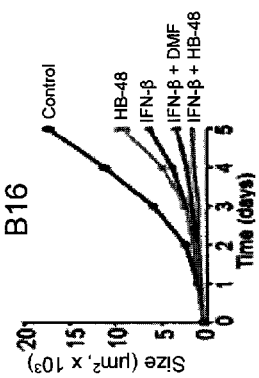
Figure 4B:
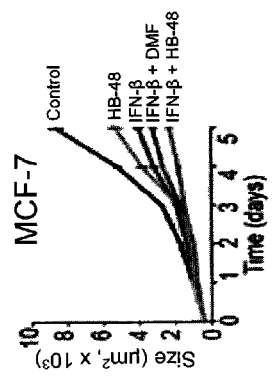
Figure 4C:
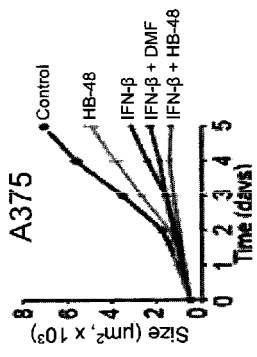
Figure 4D:
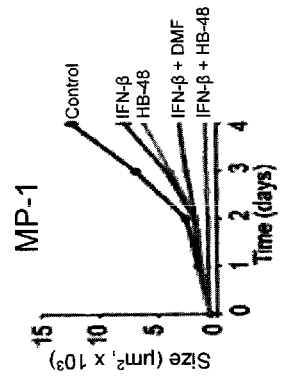

In conclusion, the results of FIGS. 1, 2 and 3 show that HB-48, when administered alone, can effectively inhibit the malignant growth of solid tumors and leukemia.

FIG. 4(A-G)—Detection of the effect of HB-48 and IFNβ on the size of solid tumor and leukemia cell clones in 3D culture conditions. FIGS. 4A through 4G show the clone size (y-axis) of the indicated tumor cells after treatment with a Control, IFN-β, HB-48, IFN-β and HB-48, or IFN-β and DMF as indicated in the figure. All cells were grown in 3D culture conditions. FIG. 4A shows the clone size of A375 cells (human melanoma cell line). FIG. 4B shows the clone size of B16 cells (mouse melanoma cell line). FIG. 4C shows the relative clone size of MP-1 cells. FIG. 4D shows the relative clone size of MCF-7 cells (human breast cancer cell line). FIG. 4E shows the relative clone size of HL-60 cells (human leukemia cell line). FIG. 4F shows the relative clone size of K562 cells (human leukemia cell line). FIG. 4G shows the relative clone size of ALL-1 cells.

FIG. 5(A-G)—The effect of HB-48 and IFN-β on the clone number of solid tumor and leukemia cells in a 3D culture system. FIGS. 5A through 5G show the number of colonies (y-axis) of the indicated tumor cells after treatment with a Control, IFN-β, HB-48, IFN-β and HB-48, or IFN-β and DMF as indicated in the figure. FIG. 5A shows treatment of A375 cells (human melanoma cell line). FIG. 5B shows treatment of B16 cells (mouse melanoma cell line). FIG. 5C shows treatment of MP-1 cells (separated from clinical melanoma patient tumor samples and could be multi-passaged). FIG. 5D shows treatment of MCF-7 cells (human breast cancer cell line). FIG. 5E shows treatment of HL-60 cells (human leukemia cell line). FIG. 5F shows treatment of K562 cells (human leukemia cell line). FIG. 5G shows treatment of ALL-1 cells.

FIG. 6(A-N)—The effect of HB-48 and IFN-β on apoptosis of solid tumor and leukemia cells in a 3D or Flask culture systems. FIG. 6 shows the amount of apoptosis (y-axis, Apoptosis rate (%)) of the indicated cancer cells after treatment with (1) Control, (2) IFN-β, (3) IFN-β and DMF, (4) HB-48 or (5) IFN-β and HB-48 as indicated on the x-axis. Cells were grown in a 3D culture system (as indicated on the bottom of the left panels) or in a flask (as indicated on the bottom of the right panels). FIG. 6A and FIG. 6B show the apoptotic rate of B16 cells (mouse melanoma cell line). FIG. 6C and FIG. 6D show the apoptotic rate of A375 cells (human melanoma cell line). FIG. 6E and FIG. 6F show the apoptotic rate of MP-1 cells. FIG. 6G and FIG. 6H show the apoptotic rate of MCF-7 cells (human breast cancer cell line). FIG. 6I and FIG. 6J show the apoptotic rate of K562 (human leukemia cell line). FIG. 6K and FIG. 6L show the apoptotic rate of HL-60 (human leukemia cell line). FIG. 6M and FIG. 6N show the apoptotic rate of ALL-1.

FIG. 7(A-H)—Effect of IFN-β and HB-48 on solid tumor-bearing mice. FIGS. 7A, 7E and 7G show the tumor size (y-axis) of NOD-SCID mice implanted with B16 tumor cells (FIG. 7A), A375 tumor cells (FIG. 7E) or MCF-7 tumor cells (FIG. 7G) and treated with Control, IFN-β, IFN-β and DMF, HB-48 or IFN-β and HB-48 as indicated in the figure. FIGS. 7B and 7H show a survival plot of survival (y-axis) vs time (Y-axis) of NOD-SCID mice implanted with B16 tumor cells and treated with Control, IFN-β, IFN-β and DMF, HB-48 or IFN-β and HB-48 as indicated in the figure. FIG. 7C shows the tumor size (y-axis) of C57 mice implanted with B16 tumor cells and treated with Control, IFN-β, IFN-β and DMF, HB-48 or IFN-β and HB-48 as indicated in the figure. FIG. 7D show a survival plot of survival (y-axis) vs time (Y-axis) of C57 mice implanted with B16 tumor cells and treated with Control, IFN-β, IFN-β and DMF, HB-48 or IFN-β and HB-48 as indicated in the figure. FIG. 7F shows tumor weight (Y-axis) of A375 tumor cells implanted in NOD-SCID mice treated with Control, IFN-β or IFN-β and HB-48 as indicated in the figure. FIG. 7G and FIG. 7H are described above.

Figure 8A:
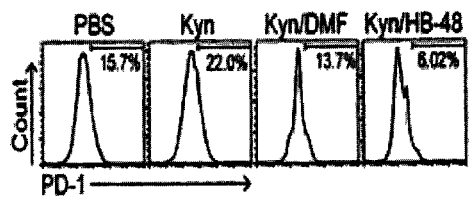
Figure 8B:
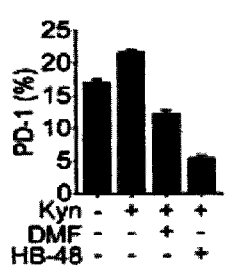
Figure 8C:
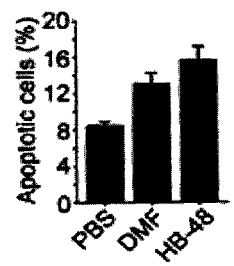

FIG. 8(A-C)—Effect of HB-48 on PD-1 expression in mouse CD8+ T cells in vitro. FIG. 8A shows a histogram derived from Fluorescence-Activated cell Sorting (FACs) of CD8+ T-cells stained for PD-1 expression after treatment with PBS, Kynurenine (Kyn), Kyn and DMF (Kyn/DMF) and Kyn and HB-48 (Kyn/HB-48) as indicated at the top of each histogram. FIG. 8B shows the results of FIG. 8A as a bar graph. FIG. 8C shows apoptosis (y-axis) of OVA-B16 cells after co-culture with OT-1 specific CD8+ T cells in the presence of PBS, DMF or HB-48 as indicated on the x-axis.

Figure 9:
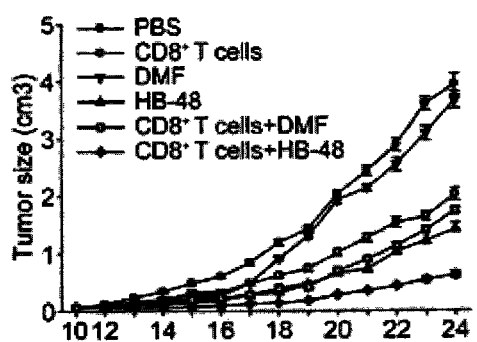

FIG. 9—Effect of HB-48 on tumor growth in vivo in the presence transferred Antigen-specific CD8+ T cells. FIG. 9 shows the treatment effect of HB-48 on adoptively transferred specific CD8+ T cells in C57 mice bearing B16-OVA cells.

FIG. 10(A-E)—Effect of HB-48 on PD-1 expression in human CD8+ T cells in vitro. FIG. 10A and FIG. 10B show the effect of HB-48 and DMF on human resting CD8+ T cells to express PD-1; FIG. 10C and FIG. 10D show the effect of HB-48 and DMF on human activated CD8+ T cells to express PD-1 in the presence of Kyn; FIG. 10E shows effect of HB-48 and DMF on human activated CD8+ T cells to express Kyn transporter PAT4 in the presence of Kyn.

FIG. 11(A-N) shows the effect of HB-48 combined with IFNβ or IFNγ on clone size of solid tumors and leukemia cells grown in 3D culture conditions. FIG. 11A and FIG. 11B show the clone size of A375 of human malignant melanoma cells treated with HB-48 combined with IFNβ or IFNγ in 3D culture conditions, and DMF combined with IFNβ or IFNγ are used as a positive control. FIG. 11C and FIG. 11D show the clone size of B16 of murine malignant melanoma cells treated with HB-48 combined with IFNβ or IFNγ in 3D culture conditions, and DMF combined with IFNβ or IFNγ are used as a positive control. FIG. 11E and FIG. 11F show the clone size of human malignant melanoma cell line MP-1 was treated with HB-48 combined with IFNβ or IFNγ in 3D culture conditions, and DMF combined with IFNβ or IFNγ are used as a positive control. FIG. 11G and FIG. 11H show the clone size of human breast cancer cell line MCF-7 was treated with HB-48 combined with IFNβ or IFNγ in 3D culture conditions, and DMF combined with IFNβ or IFNγ are used as s positive control. FIG. 11I and FIG. 11J show the clone size of human leukemia cell line HL-60 was treated with HB-48 combined with IFNβ or IFNγ in 3D culture conditions, and DMF combined with IFNβ or IFNγ are used as a positive control. FIG. 11K and FIG. 11L show the clone size of human leukemia cell line K562 was treated with HB-48 combined with IFNβ or IFNγ in 3D culture conditions, and DMF combined with IFNβ or IFNγ are used as a positive control. FIG. 11M and FIG. 11N show the clone size of human leukemia cell line ALL-1 was treated with HB-48 combined with IFNβ or IFNγ in 3D culture conditions, and DMF combined with IFNβ or IFNγ are used as a positive control.

FIG. 12(A-N) shows the effect of HB-48 combined with IFNβ or IFNγ on clone number of solid tumors and leukemia cells in 3D culture conditions. FIG. 12A and FIG. 12B show the number of colonies of human malignant melanoma cells A375 treated with HB-48 combined with IFNβ or IFNγ in 3D culture conditions, and DMF combined with IFNβ or IFNγ are used as a positive control. FIG. 12C and FIG. 12D show the number of colonies of murine malignant melanoma cells B16 treated with HB-48 combined with IFNβ or IFNγ in 3D culture conditions, and DMF combined with IFNβ or IFNγ are used as a positive control. FIG. 12E and FIG. 12F show the number of colonies of human malignant melanoma cells MP-1 treated with HB-48 combined with IFNβ or IFNγ in 3D culture conditions, and DMF combined with IFNβ or IFNγ are used as a positive control. FIG. 12G and FIG. 12H show the number of colonies of human breast cancer cell line MCF-7 treated with HB-48 combined with IFNβ or IFNγ in 3D culture conditions, and DMF combined with IFNβ or IFNγ are used as a positive control. FIG. 12I and FIG. 12J show the number of colonies of human leukemia cell line HL-60 treated with HB-48 combined with IFNβ or IFNγ in 3D culture conditions, and DMF combined with IFNβ or IFNγ are used as a positive control. FIG. 12K and FIG. 12L show the number of colonies of human leukemia cell line K562 treated with HB-48 combined with IFNβ or IFNγ in 3D culture conditions, and DMF combined with IFNβ or IFNγ are used as a positive control. FIG. 12M and FIG. 12N show the number of colonies of human leukemia cells ALL-1 treated with HB-48 combined with IFNβ or IFNγ in 3D culture conditions, and DMF combined with IFNβ or IFNγ are used as a positive control.

Figure 13:
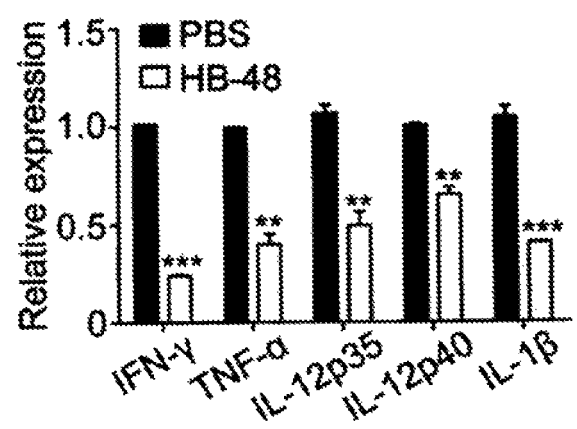

FIG. 13 shows the effect of HB-48 on the in vitro expression of inflammatory cytokines from murine macrophage isolated from mouse bone marrow.

DETAILED DESCRIPTION OF THE EMBODIMENTS

Presented herein is a novel quinochalcone (quinone chalcone) compound, and compositions thereof, for treating cancer or inflammation.

The quinochalcone compound described herein can kill differentiated tumor cells as well as cancer stem cells. In certain embodiments, the quinochalcone compound described herein displays strong anti-tumor activity, alone or in combination with an IFN. In certain embodiments, the activity of the quinochalcone compound described herein is enhanced when used with an IFN, and/or with another anti-cancer therapy. Accordingly, the a novel quinochalcone compound can be used alone, or in combination with an IFN, or in combination with another anti-cancer therapy for treating cancer. The compositions described herein, in certain embodiments, can inhibit, suppress, abrogate or terminate the growth or viability of a cancer cell, for example, a differentiated cancer cell and/or a dormant tumor stem cell. In certain embodiments, a composition described herein can kill cancer by enhancing the systemic immune response and has the advantages of high safety and minimal toxic side effects. In certain embodiments, a quinochalcone compound can stimulate an immune response by modulating immune cells such as T-cell subpopulations (e.g., CD8+ and CD4+ T cells, and regulatory T-cells), natural killer cells, macrophages, dendritic cells and enhance the anti-cancer effects of an IFN.

The quinochalcone compound described herein can also suppress the production, expression and or release of pro-inflammatory cytokines from macrophages. Accordingly, the quinochalcone compound described herein can be used alone, or in combination with another anti-inflammatory agent for treating inflammation, inflammatory conditions and/or to reduce inflammation. Also presented herein are compositions comprising a quinochalcone compound for use in treating inflammation, inflammatory conditions and/or to reduce inflammation.

Quinochalcone Compounds

In some embodiments, a quinochalcone compound comprises or consists of the structure of formula I:

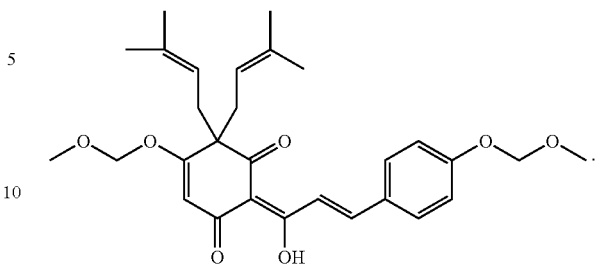

Accordingly, in some embodiments, the quinochalcone compound of structure I is referred to herein as HB-48 or as 2-[1-hydroxy-3-(4-methoxymethoxyphenyl)allylidene]-5-methoxymethoxy-6,6-diprenylcyclohex-4-ene-1,3-dione. In some embodiments, a quinochalcone compound comprises or consists of 2-[1-hydroxy-3-(4-methoxymethoxyphenyl) allylidene]-5-methoxymethoxy-6,6-diprenylcyclohex-4-ene-1,3-dione.

In certain embodiments, a quinochalcone compound, alone or in combination with an IFN, induces apoptosis, necrosis, autophagy, or death, of a cancer, a cancer cell, a malignant cell, a tumor cell, a differentiated tumor cell, a tumor stem cell or a dormant tumor stem cell. In certain embodiments, a quinochalcone compound, alone or in combination with an IFN, inhibits, suppresses, abrogates or terminates growth, viability or metastasis of a cancer, a cancer cell, a malignant cell, a tumor cell, a differentiated tumor cell, a tumor stem cell or a dormant tumor stem cell. Any suitable assay can be used to determine the ability of a quinochalcone compound to induce apoptosis, necrosis, autophagy, or death, of a cancer, a cancer cell, a malignant cell, a tumor cell, a differentiated tumor cell, a tumor stem cell or a dormant tumor stem cell. Any suitable assay can be used to determine the ability of a quinochalcone compound, in combination with an IFN, to induce apoptosis, necrosis, autophagy, or death, of a cancer, a cancer cell, a malignant cell, a tumor cell, a differentiated tumor cell, a tumor stem cell or a dormant tumor stem cell. Any suitable assay can be used to determine the ability of a quinochalcone compound to inhibit, suppress, abrogate or terminate growth, viability or metastasis of a cancer, a cancer cell, a malignant cell, a tumor cell, a differentiated tumor cell, a tumor stem cell or a dormant tumor stem cell. Any suitable assay can be used to determine the ability of a quinochalcone compound, in combination with an IFN, to inhibit, suppress, abrogate or terminate growth, viability or metastasis of a cancer, a cancer cell, a malignant cell, a tumor cell, a differentiated tumor cell, a tumor stem cell or a dormant tumor stem cell. In some embodiments, a quinochalcone compound has anti-inflammatory activity.

Any suitable method can be used to make or synthesize a quinochalcone compound. Method of making, synthesizing, and modifying small compounds such as the quinochalcone compounds described herein are described in "Organic Synthesis", Michael B. Smith, Second Edition, Copyright 2002, McGraw-Hill Higher Education; "Greene's Protective Groups in Organic Synthesis", Peter G. M. Wuts, Fifth Edition, Copyright 2014, John Wiley and Sons Inc.; and "The Organic Chemistry of Drug Synthesis", Vol. 7, Daniel Lednicer, Copyright 2008, John Wiley and Sons Inc. Methods of synthesizing quinochalcone compounds is also described in Chinese patent application no. CN210410220017.8, which content thereof is incorporated herein by reference.

In some embodiments, a quinochalcone compound of formula I is synthesized accordingly to the following steps: (1) Synthesis of 2-acetyl-3,5-dihydroxy-6,6-diprenylcyclohexa-2,4-dienone, (2) Synthesis of 2-acetyl-3-hydroxy-5-methoxymethyl-6,6-diprenylcyclohexa-2,4-dienone, (3) Synthesis of quinochalcone with a isopentenyl and methoxymethyl (MOMO), and (4) Synthesis of quinochalcone with a isopentenyl by removing the methoxymethyl (MOMO).

One example of a synthesis scheme for HB-48 is shown below.

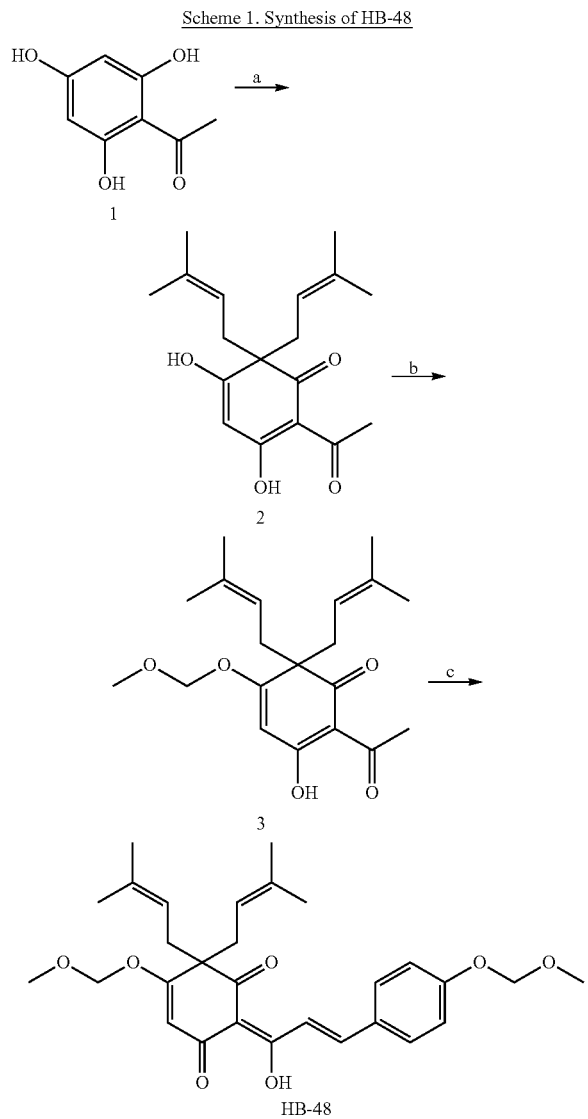

Scheme 1. Synthesis of HB-48

Reagents and conditions: (a) prenyl bromide, KOH, H₂O; (b) MOMCl, K₂CO₃, acetone, rt, 5 h; (c) 4-MOM benzaldehyde, 50% KOH, EtOH In reference to the exemplary synthesis shown above, the cyclohexenones are synthesized first, followed by methoxymethoxylation and Claisen-Schmidt condensation, where the target product (HB-48) is finally obtained. The synthesis starts with 2,4,6-trihydroxyacetophenone (1) which is prenylated with a 2 mol equivalent of prenyl bromide in aqueous potassium hydroxide to generate 2-acetyl-3,5-dihydroxy-6,6-diprenylcyclohexa-2,4-dienone (2). Then, (3) is prepared by methoxymethoxylation of (2) with chloromethyl methyl ether. Finally, (3) is mixed with 4-methoxymethoxy benzaldehyde in potassium hydroxide aqueous solution to generate HB-48.

IFN

In certain embodiments, a composition described herein comprises an Interferon (IFN). An IFN can be any naturally occurring IFN or a synthetic IFN (e.g., a recombinant IFN), or biologically active variant thereof. In some embodiments, an interferon is a Type I IFN, Type II IFN, or Type III IFN. In some embodiments, an interferon is IFN-α, IFN-β, IFN-ε, IFN-κ or IFN-ω. In some embodiments an IFN is IFN-β. In some embodiments an IFN is IFN-γ. In certain embodiments, a composition described herein comprises an IFN and a quinochalcone compound. IFN-β and IFN-γ are cytokines that belongs to the interferon family of signaling proteins, which are often released as part of the innate immune response to pathogens. IFN-γ is the only member of the type II class of interferons. IFN-β belongs to the type I class of interferons, which are important for defense against viral infections. In addition, type I interferons are often involved in cell differentiation and anti-tumor defenses. Following secretion, often in response to a pathogen, type I interferons can bind a homologous receptor complex and induce transcription of genes such as those encoding inflammatory cytokines and chemokines. Over-activation of type I interferon secretion is sometimes linked to autoimmune diseases. Mice deficient for IFN-β often display several phenotypes including defects in B cell maturation and increased susceptibility to viral infection. Some diseases associated with IFN-β include Relapsing-Remitting Multiple Sclerosis and Primary Progressive Multiple Sclerosis.

IFN-β can be any suitable mammalian IFN-β. In some embodiments, IFN-β is a Human IFN-β, or a biologically active variant thereof. Non-limiting examples of IFN-β include Human IFN-β (UniProtKB accession no. P01574), mouse IFN-β (UniProtKB accession no. P01575), rat IFN-β (UniProtKB accession no. P70499), cat IFN-β (UniProtKB accession no. Q9N2J0), horse IFN-β (UniProtKB accession no. P05012), chicken IFN-β (UniProtKB accession no. Q90873), bovine IFN-β (UniProtKB accession no. P01578), the like, natural and artificial variants thereof and combinations thereof. In some embodiments an amino acid sequence of IFN-β, or an amino acid sequence of a variant of IFN-β comprises an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to native or naturally occurring mammalian IFN-β described herein. For example, an amino acid sequence of IFN-β, or an amino acid sequence of a variant of IFN-β comprises an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to an amino acid sequence of Human IFN-β (UniProtKB accession no. P01574), mouse IFN-β (UniProtKB accession no. P01575), rat IFN-β (UniProtKB accession no. P70499), cat IFN-β (UniProtKB accession no. Q9N2J0), horse IFN-β (UniProtKB accession no. P05012), chicken IFN-β (UniProtKB accession no. Q90873), or bovine IFN-β (UniProtKB accession no. P01578).

IFN-γ can be any suitable mammalian IFN-γ. In some embodiments, IFN-γ is a Human IFN-γ, or a biologically active variant thereof. Non-limiting examples of IFN-γ include Human IFN-γ (UniProtKB accession no. P01579), mouse IFN-γ (UniProtKB accession no. P01580), rat IFN-γ (UniProtKB accession no. P01581), the like, natural and artificial variants thereof and combinations thereof. In some embodiments an amino acid sequence of IFN-γ, or an amino acid sequence of a variant of IFN-γ comprises an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to a native or naturally occurring mammalian IFN-γ described herein. For example, an amino acid sequence of IFN-γ, or an amino acid sequence of a variant of IFN-γ comprises an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to an amino acid sequence of Human IFN-γ (UniProtKB accession no. P01579), mouse IFN-γ (UniProtKB accession no. P01580), rat IFN-γ (UniProtKB accession no. P01581).

In some embodiments, a variant of IFN is a biologically active variant of IFN. A biologically active variant of IFN is an IFN, or portion thereof, and/or variant thereof, that retains at least 50%, at least 60%, at least 70%, at least 80%, at least 90%, at least 95% or 100% of the biological activity of a naturally occurring or recombinant IFN (e.g., a human IFN, e.g., human IFN-β or human IFN-γ). The biological activity of an IFN can be assess by one of skill in the art using routine biological assays. A biologically active variant of an IFN may comprise amino acid substitutions, amino acid deletions or amino acid insertions, wherein the IFN variant retains at least 50%, at least 60%, at least 70%, at least 80%, at least 90%, at least 95% or 100% of the biological activity of its native parent, naturally occurring parent, or unmodified parent IFN. A biologically active variant of IFN may comprise a portion of another protein. In some embodiments, a biologically active variant of IFN is a fusion protein of an IFN, or a biologically active portion thereof, and another protein or peptide. For example, an IFN, or a biologically active portion thereof, can be fused to an antibody, a portion of an antibody (e.g., an Fc region of an antibody) or a portion of another cytokine using recombinant technology.

In certain embodiments, an IFN, or a biologically active variant thereof, comprises one or more modified amino acids, amino acid analogues or amino acid variants. In certain embodiments, a modified amino acid includes one or more amino acids having a side chain, N-terminus, or C-terminus that is chemically altered or derivatized. Non-limiting examples of modified amino acids include amino acids modified by acetylation, acylation, phosphorylation, glycosylation, myristoylation, amidation, hydroxylation (e.g., aspartic acid/asparagine hydroxylation), phosphopantethane attachment, methylation, methylthiolation, prenylation, addition of an intein, ADP-ribosylation, bromination, citrullination, deamination, dihydroxylation, formylation, geranyl-geranylation, glycation or palmitoylation. Non-limiting examples of amino acid analogues include D-amino acids, β-amino acids, α-amino-n-butyric acid, norvaline, dehydroalanine, norleucine, alloisoleucine, t-leucine, α-amino-n-heptanoic acid, pipecolic acid, α,β-diaminopropionic acid, α,γ-diaminobutyric acid, ornithine, allothreonine, homocysteine, homoserine, β-alanine, β-amino-n-butyric acid, β-aminoisobutyric acid, γ-aminobutyric acid, α-aminoisobutyric acid, isovaline, sarcosine, N-ethyl glycine, N-propyl glycine, N-isopropyl glycine, N-methyl alanine, N-ethyl alanine, N-methyl β-alanine, N-ethyl β-alanine, isoserine, and α-hydroxy-γ-aminobutyric acid. An IFN or a biologically active variant thereof may include one or more D-amino acids substituted for L-amino acids. In certain embodiments, an IFN or a biologically active variant thereof comprises one or more amino acid analogues and/or unnatural amino acids. In some embodiments, an IFN or a biologically active variant thereof comprises one or more bulk amino acids, or bulk aromatic amino acids, non-limiting examples of which include Dip (3,3-diphenylalanine), Bip (biphenylalanine), Ath (9-anthracenylalanine), Nal (1-naphthylalanine), Dap (2,3-diaminopropionic acid) and Dab (2,4-diaminobutanoic acid). In certain embodiments, one or more modified amino acid, amino acid analogues, amino acid variants, D-amino acids, bulk amino acids or synthetic amino acids are introduced into an IFN or a biologically active variant thereof, to increase the in vivo stability or half-life of the IFN, or variant thereof.

In some embodiments an IFN or a biologically active variant thereof, is derived, produced, obtained, isolated, and/or purified from a suitable species. In some embodiments an IFN or a biologically active variant thereof, is derived, produced, obtained, isolated, and/or purified from a suitable mammal, non-limiting examples of which include a primate, a human, a rabbit, goat, horse, cow, rat, mouse, and llama, for example. In certain embodiments, an IFN or a biologically active variant thereof, is a recombinant protein. Accordingly, in certain embodiments, an IFN or a biologically active variant thereof, is expressed, isolated, and/or purified from a suitable expression system, non-limiting examples of which include a suitable bacteria, phage, insect, virus, plant, bird, fish or mammalian expression system. For example, a nucleic acid encoding an IFN or a biologically active variant thereof, can be introduced into a suitable mammalian cell line that expresses and secretes the IFN or the biologically active variant thereof, into the cell culture media. In certain embodiments, an IFN or a biologically active variant thereof, is derived, produced, obtained, isolated, and/or purified from a bird (e.g., from a chicken egg, or a bird egg). In some embodiments an IFN or a biologically active variant thereof, is derived, produced, obtained, isolated, and/or purified from a plant (e.g., by a genetically engineered plant). In some embodiments an IFN or a biologically active variant thereof, is produced, obtained, isolated, or purified from a prokaryotic or eukaryotic cell (e.g., produced by a genetically engineered bacteria). In some embodiments an IFN or a biologically active variant thereof, is produced, obtained, isolated, or purified from a suitable virus (e.g., produced by a genetically engineered virus).

Nucleic acids, or portions thereof, that encode an IFN or a biologically active variant thereof, may be cloned, subcloned, rearranged or modified for recombinant expression by a suitable cloning procedure and subsequently expressed using a suitable expression system by a method known to those skilled in the art (e.g., see Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987, including supplements 1 to 120 thereof, and annual updates); and Methods in molecular biology, edited by Benny K. C. Lo, Springer Science & Business Media, (2004)).

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, Vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences.

Distinguishable Identifiers

In some embodiments, a quinochalcone compound, IFN, or a variant thereof, is conjugated to one or more distinguishable identifiers. Accordingly, in some embodiments, a quinochalcone compound comprises one or more distinguishable identifiers. Any suitable distinguishable identifier can be conjugated to a quinochalcone compound. In some embodiments, a quinochalcone compound is conjugated to a distinguishable identifier to determine the in vivo pharmacokinetic properties and/or bioavailability of a quinochalcone compound. In certain embodiments a distinguishable identifier can be directly or indirectly associated with (e.g., bound to) a quinochalcone compound. For example, a distinguishable identifier can be covalently or non-covalently bound to a quinochalcone compound. In some embodiments a distinguishable identifier is reversibly associated with a quinochalcone compound. In certain embodiments a distinguishable identifier that is reversibly associated with a quinochalcone compound can be removed from a quinochalcone compound using a suitable method (e.g., by increasing salt concentration, denaturing, washing, adding a suitable solvent and/or by heating).

In some embodiments a distinguishable identifier is a detectable label, non-limiting examples of which include a radiolabel (e.g., an isotope), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme; e.g., alkaline phosphatase and horseradish peroxidase), an antibody or part thereof (e.g., an Fc portion), an antigen or part thereof (e.g., for detection with a suitable antibody), a linker, a member of a binding pair (e.g., biotin-avidin, antibody-antigen, and the like), an enzyme substrate, a small molecule (e.g., biotin, avidin), a mass tag, quantum dots, nanoparticles, the like or combinations thereof. Any suitable fluorophore can be used as a detectable label. A detectable label can be detected and/or quantitated by a variety of suitable techniques thereby allowing tracking, detection and quantitation of a quinochalcone compound. Accordingly, in some embodiments, a composition disclosed herein comprises a quinochalcone compound comprising a distinguishable identifier.

Subjects

The term "subject" refers to animals, typically mammalian animals. In some embodiments a subject is a mammal. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, and pigs) and experimental animals (e.g., mouse, rat, rabbit, and guinea pig). In some embodiments, a subject is a primate. In some embodiments a subject is a non-human primate. In some embodiments a subject is a human. A mammal can be any age or at any stage of development (e.g., an adult, teen, child, infant, or a mammal in utero). A mammal can be male or female. In certain embodiments a mammal can be an animal disease model, for example, animal models used for the study of cancer or inflammation.

In certain embodiments a subject has or is suspected of having a cancer. In certain embodiments a subject is at risk of developing a cancer. Subjects at risk of developing a cancer can be subjects in high-risk groups who can be identified by a medical professional. Non-limiting examples of subjects at risk of cancer include chronic smokers, overweight individuals, human subjects over the age of 60, subjects with a family history of cancer, subjects having certain gene mutations that are associated with certain cancers, subjects infected with, or previously infected with certain viruses associated with the development of certain cancers, subjects exposed to known carcinogens, subjects exposed to excessive radiation (e.g., UV radiation, alpha, beta, or gamma radiation), subjects having chronic inflammation, the like, or combinations thereof. In some embodiments a subject or mammal is "at risk" of cancer metastasis. Certain cancers are known to be metastatic or have a high probability of metastasis depending on the cancer type, stage, tissue or origin, and/or age, sex or health condition of a subject. Metastatic disease typically occurs when patients show relapse after standard of care therapy. A subject at risk can be readily identified by a medical professional (e.g., a doctor, or an oncologists).

In certain embodiments a subject has or is suspected of having inflammation or an inflammatory condition.

Methods of Treatment

A quinochalcone compound described herein can be used to treat inflammation and/or cancer. In some embodiments, a method described herein comprises a method of treating inflammation in a subject who has, or is suspected of having inflammation or an inflammatory condition. In certain embodiments, a method of treating inflammation comprises blocking, inhibiting, ameliorating, abrogating, or suppressing inflammation (e.g., inflammation in a subject). In certain embodiments, a method of treating inflammation comprises inhibiting, reducing the severity of, delaying the onset of, suppressing, ameliorating, or abrogating one or more symptoms associate with inflammation. In certain embodiments, a method of treating inflammation comprises prolonging or sustaining life, or improving the quality of life of a subject having inflammation, compared to the length or quality of life that the subject would have in the absence of a, inflammation treatment described herein.

In some embodiments, a method of treating inflammation in a subject comprises administering to the subject a therapeutically effective amount of a quinochalcone compound to the subject. In some embodiments, a method of treating inflammation in a subject comprises administering to a subject in need thereof a therapeutically effective amount of a quinochalcone compound. Accordingly, in certain embodiments, a method of treating inflammation in a subject comprises, (a) providing a subject having or suspected of having inflammation or an inflammatory condition, and (b) administering to the subject a therapeutically effective amount of a quinochalcone compound. In certain embodiments, a method of treating inflammation in a subject comprises, (a) providing a subject having or suspected of having inflammation or an inflammatory condition, and (b) administering to the subject a therapeutically effective amount of a quinochalcone compound, alone or in combination with an inflammatory agent, non-limiting examples of which include a nonsteroidal anti-inflammatory drug (NSAID), an analgesic (e.g., a non-narcotic analgesic or an opioid narcotic), a corticosteroid, disease-modifying anti-rheumatic drugs (DMARDs), for example methotrexate, hydroxychloroquine, leflunomide, sulfasalazine, JAK inhibitors and the like, and biologics.

In some embodiments, a method described herein comprises a method of treating a cancer in a subject that has, or is suspected of having, a cancer. In certain embodiments, a method of treating a cancer comprises blocking, inhibiting, ameliorating, abrogating, or suppressing growth, metastasis or viability of a cancer (e.g., cancer cells, e.g., a tumor). In some embodiments, a method of treating a cancer comprises a method of inhibiting, blocking, ameliorating, reducing or suppressing growth or viability of a cancer in a subject. In some embodiments, a method of treating a cancer comprises inhibiting, blocking, ameliorating, reducing or suppressing metastasis of a cancer in a subject. In certain embodiments, a method of treating a cancer in a subject comprises an attempt to inhibit, block, ameliorate, reduce or suppress growth, viability or metastasis of a cancer in a subject, with a reasonable expectation of success. In certain embodiments, a method of treating a cancer comprises inducing necrosis, death or apoptosis of one or more cancer cells in a subject. In certain embodiments, a method of treating a cancer comprises inhibiting, reducing the severity of, delaying the onset of, suppressing, ameliorating, or abrogating one or more symptoms associate with a cancer. In certain embodiments, a method of treating a cancer comprises prolonging or sustaining life, or improving the quality of life of a subject having a cancer, compared to the length or quality of life that the subject would have in the absence of a cancer treatment.

In some embodiments, a method of treating a subject comprises administering to a subject in need thereof a therapeutically effective amount of a quinochalcone compound and/or a therapeutically effective amount of an IFN, or a biologically active variant thereof. In some instances a cancer in a subject may become resistant to an anti-cancer therapy, non-limiting examples of which include treatment with IFN-β, treatment with IFN-γ, surgical dissection of a cancer, treatment with a chemotherapeutic agent, treatment with immunotherapy, treatment with an anti-cancer vaccine, treatment with radiation, the like and combinations thereof. Therefore, in some embodiment, a quinochalcone compound may be administered to supplement and/or enhance the activity of an IFN or another anti-cancer therapy. Accordingly, in certain embodiments, a method of treating a subject comprises, (a) providing a subject undergoing treatment with, or previously treated with, an anti-cancer therapy, and (b) administering to the subject a therapeutically effective amount of a quinochalcone compound, alone or in combination with a therapeutically effective amount of an IFN, or a biologically active variant thereof. In certain embodiments, a method of treating a subject comprises, (a) providing a subject having or suspected of having a cancer, wherein the subject is resistant to, or unresponsive to, treatment with an anti-cancer therapy, and (b) administering to the subject a therapeutically effective amount of a quinochalcone compound, alone or in combination with a therapeutically effective amount of an IFN, or a biologically active variant thereof. In some embodiments, a method of treating a subject comprises administering to the subject a therapeutically effective amount of a quinochalcone compound or composition described herein and a therapeutically effective amount of one or more other active pharmaceutical ingredients (API).

In some embodiments, a quinochalcone compound, or a composition comprising a quinochalcone compound as the sole active pharmaceutical ingredient (API), is administered to a subject having or suspected of having a cancer. In some embodiments, a quinochalcone compound and an IFN, or a biologically active variant thereof, are administered to a subject having or suspected of having a cancer. In certain embodiments, a quinochalcone compound and an IFN, or a biologically active variant thereof, are administered to a subject at substantially the same time. In some embodiments, a quinochalcone compound and an IFN, or a biologically active variant thereof, are administered to a subject at different times. In certain embodiments, a quinochalcone compound and an IFN, or a biologically active variant thereof, are administered within 5 minutes, within 10 minutes, within 15 minutes, within 30 minutes, within 45 minutes, within 60 minutes, or within 120 of each other. In certain embodiments, a quinochalcone compound and an IFN, or a biologically active variant thereof, are administered within 1 hour, within 2 hours, within 3 hours, within 4 hours, within 5 hours, within 6 hours, within 8 hours, within 10 hours, within 12 hours or within 24 hours of each other. In certain embodiments, a quinochalcone compound and an IFN, or a biologically active variant thereof, are administered within 1 to 3 days of each other, or within 1, 2 or 3 days of each other.

In certain embodiments, a method of treating a cancer in a subject comprises administering a therapeutically effective amount of a quinochalcone compound and/or a therapeutically effective amount of an IFN, or a biologically active variant thereof, to a subject in need thereof, in combination with another anti-cancer therapy, non-limiting examples of which include a T-cell activating agent, an adjuvant, an anti-cancer vaccine, a radiation treatment, an immunotherapy (e.g., anti-HER2, or anti-CD20), a chemotherapy, and the like or combinations thereof. In some embodiments, a T-cell activating agent is an antibody that binds to CD3, OX40, GITR, CD137 (41BB), CD27, HVEM, LAG-3, TIM3, VISTA or BTLA.

Any suitable chemotherapeutic agent can be used for a method described herein. In some embodiments a chemotherapeutic agent comprises or consists of an alkylating agent, an anthracycline, cytoskeletal disruptors, epothilones (e.g., epothilone), histone deacetylase inhibitors (e.g., vorinostat, romidepsin), inhibitors of topoisomerase I (e.g., irinotecan, topotecan), inhibitors of topoisomerase II (e.g., etoposide, teniposide, tafluposidean), kinase inhibitors, peptide antibiotics (e.g., bleomycin, actinomycin), platinum-based agents (e.g., carboplatin, cisplatin, oxaliplatin), compounds targeting DNA repair enzyme poly-ADP ribose polymerase-1, Parp inhibitors, retinoids (e.g., tretinoin, alitretinoin, bexarotene), vinca alkaloids and compounds (e.g., vinblastine, vincristine, vindesine, vinorelbine), anti-metabolites, plant extracts, plant alkaloids, nitrosourea, hormone, nucleoside or nucleotide analog and combinations thereof.

In some embodiments, a chemotherapeutic agent comprises an alkylating anti-neoplastic agent (e.g., an alkylating anti-neoplastic agent). An alkylating antineoplastic agent is a class of chemotherapeutic agents that work, in part, by attaching an alkyl group (e.g., CnH2n+1) to DNA, a process known as alkylation. Some alkylating antineoplastic agents are administered as a pro-drug that is converted in vivo to an active alkylating agent. An alkylating antineoplastic agent often alkylates a guanine base of DNA. Alkylating antineoplastic agents are most effective on proliferating cells (e.g., cancer cells) which, in general, proliferate faster and with less error-correcting than healthy cells. Non-limiting examples of alkylating anti-neoplastic agents include Altretamine (hexamethylmelamine, HEXALEN®), Busulfan, Carmustine (BCNU), Chlorambucil, Cyclophosphamide, Dacarbazine (DTIC), Fotemustine, Ifosfamide, Lomustine (CCNU), Mechlorethamine, Melphalan, Procarbazine, semustine (MeCCNU), Streptozotocin, Temozolomide, Thiotepa (triethylenethio-phosphoramide), Carboplatin, Cisplatin, Oxaliplatin, monofunctional alkylators, nitrosoureas, temozolomide, the like or combinations thereof.

In some embodiments, a chemotherapeutic agent comprises a DNA intercalating agent which is often an agent that attaches or binds to DNA or RNA. Non-limiting examples of a DNA intercalating agent include acrolein, anthracycline, phosphoramide, Actinomycin D, bleomycin, idarubicin, daunorubicin, doxorubicin, elsamicin A, epirubicin, ethidium, m-AMSA, mitoxantrone, doxorubicin (Adriamycin, Doxil, Myocet, hydroxydaunorubicin, hydroxydaunomycin), Epirubicin, Idarubicin, Valrubicin, TAS-103, MLN944 (XR5944), Obatoclax, mechlorethamine, methotrexate, 6-mercaptopurine, thioguanine, 5-fluorouracil, cytosine arabinoside, 5-azacytidine (5-AZC) and 5-azacytidine related compounds, mithramycin, mitomycin C, hydroxyurea, carboplatin, oxiplatin, mitotane, a taxane, vinblastine, vincristine, dibromomannitol, gemcitabine, pemetrexed, the like or a combination thereof.

In some embodiments, a chemotherapeutic agent comprises a cytoskeletal disruptor. Non-limiting examples of cytoskeletal disruptors (e.g., taxanes) include paclitaxel, taxol, and docetaxel.

In some embodiments, a chemotherapeutic agent comprises a kinase inhibitor. Non-limiting examples of kinase inhibitors include bortezomib, erlotinib, gefitinib, imatinib, vemurafenib, vismodegib, the like, analogs and compounds thereof.

In some embodiments, a chemotherapeutic agent comprises one or more nucleotide analogs. Non-limiting examples of nucleotide analogs include azacitidine, azathioprine, capecitabine, cytarabine, doxifluridine, fluorouracil, gemcitabine, hydroxyurea, mercaptopurine, methotrexate, tioguanine (formerly thioguanine), the like, analogs and compounds thereof.

In some embodiments, a chemotherapeutic agent comprises one or more molecules that target DNA repair enzyme poly-ADP ribose polymerase-1 (PARP) and inhibit DNA repair. Non-limiting examples of PARP inhibitors are olaparib, rucaparib, niraparib, veliparib, talazoparib and the like, analogs and compounds thereof.

Cancers & Metastasis

In some embodiments, a method or composition (e.g., a pharmaceutical composition) disclosed herein is used for treating a subject having or suspected of having a cancer. In some embodiments, a quinochalcone compound, alone or in combination with an IFN, is used for treating a subject having or suspected of having a cancer. In some embodiments, a cancer is a neoplasm, tumor or neoplastic disorder. In certain embodiments, a cancer is a malignant cancer. A cancer may be metastatic or non-metastatic. Non-limiting examples of a cancer that can be treated by a method herein include a carcinoma, sarcoma, neuro neoplasia, lymphoma, myeloma, leukemia, melanoma, mesothelioma, solid or soft tissue tumors, and secondary cancers (e.g., derived from a primary site)). Non-limiting examples of a carcinoma include respiratory system carcinomas, gastrointestinal system carcinomas, genitourinary system carcinomas, testicular carcinomas, prostatic carcinomas, endocrine system carcinomas, basal cell carcinoma of the skin, carcinoma of unknown primary, cholangiocarcinoma, ductal carcinoma in situ (DCIS), merkel cell carcinoma, lung carcinoma, thymoma and thymic carcinoma, midline tract carcinoma, lung small cell carcinoma, thyroid carcinoma, liver hepatocellular carcinoma, squamous cell carcinoma, head and neck squamous carcinoma, breast carcinoma, epithelial carcinoma, adrenocortical carcinoma, ovarian surface epithelial carcinoma, and the like, further including carcinomas of the uterus, cervix, colon, pancreas, kidney, esophagus, stomach and ovary. Non-limiting examples of a sarcoma include Ewing sarcoma, lymphosarcoma, liposarcoma, osteosarcoma, soft tissue sarcoma, Kaposi sarcoma, rhabdomyosarcoma, uterine sarcoma, chondrosarcoma, leiomyosarcoma, fibrosarcoma and the like. Non-limiting examples of a neuro neoplasia include glioma, glioblastoma, meningioma, neuroblastoma, retinoblastoma, astrocytoma, oligodendrocytoma and the like. Non-limiting examples of lymphomas, myelomas, and leukemias include acute and chronic lymphoblastic leukemia, myeloblastic leukemia, multiple myeloma, poorly differentiated acute leukemias (e.g., erythroblastic leukemia and acute megakaryoblastic leukemia), acute promyeloid leukemia (APML), acute myelogenous leukemia (AML), chronic myelogenous leukemia (CML), acute lymphoblastic leukemia (ALL), which includes B-lineage ALL and T-lineage ALL, chronic lymphocytic leukemia (CLL), prolymphocytic leukemia (PLL), hairy cell leukemia (ELL), Waldenstrom's macroglobulinemia (WM), non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Non-limiting examples of soft or solid tissue tumors include visceral tumors, seminomas, hepatomas, and other tumors of the breast, liver, lung, pancreas, uterus, ovary, testicle, head, neck, eye, brain, mouth, pharynx, vocal cord, ear, nose, esophagus, stomach, intestine, colon, adrenal, kidney, bone, bladder, urethra, carcinomas, lung, muscle, skin, feet, hands, and soft tissue.

Inflammation

Disclosed herein are methods and uses of treating a subject having or suspected of having inflammation or an inflammatory condition. An inflammatory condition can be a pro-inflammatory condition or an autoimmune disorder. Non-limiting examples of an autoimmune disorder or pro-inflammatory condition include polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatic, Spondyloarthritides, Pulmonary arterial hypertension, graft-versus-host disease, autoimmune myocarditis, contact hypersensitivity (contact dermatitis), gastro-esophageal reflux disease, erythroderma, Behcet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility and immune-mediated infertility.

In some embodiments, inflammation is associated with pain and/or swelling. Accordingly, a quinochalcone compound can be used to treat pain and/or swelling.

Compositions, Administration and Dosing

In some embodiments, a composition comprises a quinochalcone compound. In some embodiments, a composition comprises a quinochalcone compound and an IFN. In certain embodiments, a composition described herein is a pharmaceutical composition suitable for administration to a human. In some embodiments, a pharmaceutical composition comprises one or more suitable pharmaceutical excipients and/or carriers.

A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In certain embodiments a composition or pharmaceutical composition comprises a suitable formulation material, diluent, excipient or additive described in "Remington: The Science And Practice Of Pharmacy" Mack Publishing Co., Easton, Pa., 19$^{th}$ Edition, (1995) (hereafter, "Remington '95"), or "Remington: The Science And Practice Of Pharmacy", Pharmaceutical Press, Easton, Pa., 22$^{nd}$ Edition, (2013) (hereafter, "Remington 2013"). In certain embodiments a composition or pharmaceutical composition described herein is made by a process described in Remington '95 and/or Remington 2013.

In certain embodiments, a pharmaceutical composition comprises a suitable excipient, non-limiting examples of which include additives, salts, anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keeps a pharmaceutical mixture combined. Suitable binders for making pharmaceutical formulations are often used in the preparation of pharmaceutical tablets, capsules, granules, aerosols, powders, and suppositories, for example, are known to those skilled in the art.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide compound, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycolpolyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a composition or pharmaceutical composition is substantially free of contaminants (e.g., blood cells, platelets, polypeptides, minerals, blood-borne compounds or chemicals, virus, bacteria, other pathogens, toxin, and the like). In some embodiments a composition or pharmaceutical composition is substantially free of serum and serum contaminants (e.g., serum proteins, serum lipids, serum carbohydrates, serum antigens and the like). In some embodiments a composition or pharmaceutical composition is substantially free of a pathogen (e.g., a virus, parasite or bacteria). In some embodiments a composition or pharmaceutical composition is substantially free of endotoxin. In some embodiments a composition or pharmaceutical composition is sterile. In certain embodiments, a composition or pharmaceutical composition comprises a quinochalcone compound and a suitable diluent (e.g., phosphate buffered saline).

The pharmaceutical compositions described herein may be conFig.d for administration to a subject in any suitable form and/or amount according to the therapy in which they are employed. For example, a pharmaceutical composition conFig.d for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), and the like). In certain embodiments, reconstituted forms of a lyophilized pharmaceutical composition are suitable for parenteral administration (e.g., intravenous administration) to a mammal.

In certain embodiments, a pharmaceutical composition is conFig.d for oral administration and may be formulated as a tablet, microtablet, minitablets, micropellets, powders granules, capsules (e.g., capsules filled with microtablets, micropellets, powders or granules), emulsions or solutions. Pharmaceutical compositions conFig.d for oral administration may comprise suitable coatings to delay or sustain release of the active ingredient (e.g., a binding agent), non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical composition described herein may be conFig.d for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a binding agent from a topical patch.

In some embodiments a pharmaceutical composition described herein is formulated as a suppository.

In certain embodiments, an optimal pharmaceutical composition will be determined by one skilled in the art depending upon, for example, the intended route of administration, delivery format and desired dosage (see e.g., Remington '95 or Remington 2013, supra). In certain embodiments, such compositions may influence the physical state, stability, rate of in vivo release and rate of in vivo clearance of the antibody drug conjugates of the disclosure. A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

In some embodiments, presented herein is a composition or pharmaceutical composition for use as a medicament for the treatment of cancer or a neoplastic disorder in a subject, wherein the composition or pharmaceutical composition comprises a quinochalcone compound described herein. In some embodiments, presented herein is a composition or pharmaceutical composition comprising a quinochalcone compound described herein for use in the treatment of cancer or a neoplastic disorder.

Route

In some embodiments, a quinochalcone compound and an IFN are administered to a subject by a suitable route of administration. In some embodiments, a composition described herein is administered to a subject by a suitable route of administration. A route of administration can be chosen by an individual care-giver or physician in view of a patient's condition. In some embodiments, a route of administration used herein is a route disclosed in, or taught in Fingl et al. 1975, in "The Pharmacological Basis of Therapeutics", which is incorporated herein by reference in its entirety. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intraarticular, into a joint space, intracardiac (into the heart), intracavernous injection, intralesional (into a skin lesion), intraosseous infusion (into the bone marrow), intrathecal (into the spinal canal), intrauterine, intravaginal, intratumoral (i.e., intratumor), intravesical infusion, intravitreal), the like or combinations thereof.

In some embodiments a quinochalcone compound, and/or an IFN, or a composition described herein is provided to a subject for self-administration or for administration to the subject by another (e.g., a care-giver). For example a composition described herein can be provided with an instruction written by a medical practitioner that authorizes a patient to be provided a composition or treatment described herein (e.g., a prescription). In another example, a composition can be provided to a subject wherein the subject self-administers a composition orally, intravenously, topically or by way of an inhaler, for example.

Formulations

One or more compositions (e.g., pharmaceutical compositions) can be formulated to be compatible with a particular route of administration or use. Compositions for parenteral, intradermal, or subcutaneous administration can include a sterile diluent, such as water, saline solution, fixed oils, polyethylene glycols, glycerin, propylene glycol or other synthetic solvents. A pharmaceutical composition may contain one or more preservatives to prevent microorganism growth (e.g., antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose). Antibacterial and antifungal agents include, for example, parabens, chlorobutanol, phenol, ascorbic acid and thimerosal.

In some embodiments, a quinochalcone compound, an IFN or combination thereof are formulated, alone or in combination, as a lyophilized powder. In some embodiments, a pharmaceutical composition described herein is formulated as a lyophilized powder. In certain embodiments, a lyophilized powder is formulated for reconstitution in a solvent that is suitable for injection into a mammal (e.g., a human). In certain embodiments, a lyophilized powder is formulated for oral administration, for example in the form of a granular powder or microparticles filled into capsules or compressed into tablets.

Compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. In some embodiments, a pharmaceutical composition includes an agent that delays absorption, for example, aluminum monostearate and gelatin which can prolong absorption of injectable compositions. In some embodiments, a pharmaceutical composition comprises polysorbate 20 or polysorbate 80, for example, up to 1%. Other non-limiting additives include histidine HCl, and α,α-trehalose dehydrate.

In some embodiments, one can administer compositions for use according to the methods of the disclosure in a local rather than systemic manner, for example, via direct application to the skin, mucous membrane or region of interest for treating, including using a depot or sustained release formulation.

In some embodiments, active ingredients (e.g., one or more quinochalcone compounds, and/or one or more IFNs) can be administered alone or formulated as a composition (e.g., a pharmaceutical composition). In other embodiments, one or more quinochalcone compounds can be administered in combination with one or more additional materials (e.g., one or more chemotherapeutic agents or T-cell activators), for example, or as two separate compositions or as a single composition where the additional material(s) is (are) mixed or formulated together with one or more quinochalcone compounds. For example, without being limited thereto, one or more quinochalcone compounds can be formulated with additional excipients, or additional active ingredients.

The pharmaceutical compositions can be manufactured by any suitable manner, including, e.g., by means of conventional mixing, dissolving, granulating, dragee-making, levigating, emulsifying, encapsulating, entrapping or tableting processes. Pharmaceutical compositions comprising a quinochalcone compound and/or an IFN can be formulated in any suitable manner using one or more pharmaceutically acceptable carriers, non-limiting examples of which include carriers, solvents, salts, excipients, additives, preservatives, and/or auxiliaries. Proper formulation can depend upon the route of administration chosen. In particular, pharmaceutical compositions can comprise any suitable carrier, formulation, or ingredient, the like or combinations thereof as listed in Remington '95 and/or Remington 2013, the contents of which are incorporated herein by reference in their entirety. The various materials listed herein, alone or in combination, can be incorporated into or used with the materials described in Remington '95 or Remington 2013. Any suitable techniques, carriers, and excipients can be used, including those understood in the art; e.g., as described in Remington '95 or Remington 2013.

In some embodiments, a pharmaceutical composition described herein can be formulated, for example, as a topical formulation. The topical formulation may include, for example, a formulation such as a gel formulation, a cream formulation, a lotion formulation, a paste formulation, an ointment formulation, an oil formulation, and a foam formulation. The composition further may include, for example, an absorption emollient.

A composition described herein can be administered on a daily basis, on an as-needed basis, or on a regular interval such as twice daily, three times daily, every other day, etc. A composition can be administered for a period of time ranging from a single as needed administration to administration for 1 day to multiple years, or any value there between, (e.g., 1 to 90 days, 1 to 60 days, 1 to 30 days, etc.). The dosages described herein can be daily dosages or the dosage of an individual administration, for example, even if multiple administrations occur (e.g., 2 sprays into a nostril).

In some embodiments, a composition described herein can be formulated for administration into the upper respiratory track/bronchi or nasal cavities. For example a composition can be, for example, formulated as an aerosol formulation, including formulated for use in a nebulizer or an inhaler. The compositions may include, for example, one or more of dichlorodifluoromethane, trichlorofluoromethane, dichlorotetrafluoroethane, carbon dioxide, and the like. The pharmaceutical compositions can be formulated for use in a nebulizer or an inhaler, for example.

A pharmaceutical composition may comprise one or more suitable carriers. In some embodiments, a carrier includes one or more chemical compounds that facilitate the incorporation of an active ingredient (e.g., one or more quinochalcone compounds) into cells or tissues. For example dimethyl sulfoxide (DMSO) is a commonly utilized carrier as it facilitates the uptake of many compounds and peptides into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

In certain embodiments, a pharmaceutical composition comprises hydrophobic excipients, additives, or other hydrophobic components. A pharmaceutical carrier for certain hydrophobic peptides can be a co-solvent system comprising benzyl alcohol, a nonpolar surfactant, a water-miscible organic polymer, and an aqueous phase. A common co-solvent system contemplated for use herein is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of POLYSORBATE 80™; the fraction size of polyethylene glycol can be varied; other biocompatible polymers can replace polyethylene glycol, e.g., polyvinyl pyrrolidone; and other sugars or polysaccharides can substitute for dextrose.

Alternatively or additionally, other carriers can be employed, if required. Liposomes and emulsions are well known examples of delivery vehicles or carriers for hydrophobic drugs and drug compositions. Additionally, a composition described herein can be delivered using a sustained-release system, such as semipermeable matrices of solid hydrophobic polymers containing the therapeutic agent. The pharmaceutical compositions described herein can be administered to a patient per se, or in pharmaceutical compositions where they are mixed with other active ingredients, as in combination therapy, or suitable carriers or excipient(s). The compounds and compositions can be formulated with salts or excipients, such as for example, sodium or meglumine. Techniques for formulation and administration can be found in "Remington's Pharmaceutical Sciences," Mack Publishing Co., Easton, Pa., 18th edition, 1990, Remington '95 and/or Remington 2013.

Furthermore, the compounds and compositions used herein can be stable over an extended period of time, for example on the order of months or years. Compositions described herein, in some embodiments, may comprise a preservative. The preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). The preservative can comprise an alkyl-mercury salt of thiosalicylic acid, such as thiomersal, phenylmercuric nitrate, phenylmercuric acetate or phenylmercuric borate. The preservative can comprise parabens, such as methylparaben or propylparaben. The preservative can comprise an alcohol, such as chlorobutanol, benzyl alcohol or phenyl ethyl alcohol. The preservative can comprise a biguanide compound, such as chlorohexidine or polyhexamethylene biguanide. The preservative can comprise sodium perborate, imidazolidinyl urea, and/or sorbic acid. The preservative can comprise stabilized oxychloro complexes, such as known and commercially available under the trade name PURITE®). The preservative can comprise polyglycol-polyamine condensation resins, such as known and commercially available under the trade name POLYQUART® from Henkel KGaA. The preservative can comprise stabilized hydrogen peroxide generated from a source of hydrogen peroxide for providing an effective trace amount of resultant hydrogen peroxide, such as sodium perborate tetrahydrate. The preservative can be benzalkonium chloride.

The preservative can enable a composition to be used on multiple occasions. The preservative can reduce the effects of one or more of acid exposure, base exposure, air exposure, heat, and light on the active ingredient. The compounds and pharmaceutical compositions described herein can include any suitable buffers, such as for example, sodium citrate buffer and/or sequestering agents, such as edetate disodium sequestering agent. Ingredients, such as meglumine, may be added to adjust the pH of a composition or compound described herein. Compounds and compositions described herein may comprise sodium and/or iodine, such as organically bound iodine. Compositions and compounds used herein may be provided in a container in which the air is replaced by another substance, such as nitrogen.

Certain embodiments provide compositions comprising one or more active ingredients (e.g., a quinochalcone compound, IFN-β, etc.) in an amount effective to achieve its intended purpose (e.g., a therapeutically effective amount). A "therapeutically effective amount" means an amount to prevent or treat a cancer. In certain embodiments, a "therapeutically effective amount" is an amount sufficient to block, inhibit, ameliorate, abrogate, or suppress growth, metastasis or viability of a cancer (e.g., cancer cells, e.g., a tumor, a tumor cell, a differentiated tumor cell, a tumor stem cell). In certain embodiments, a "therapeutically effective amount" is an amount sufficient to induce necrosis, death or apoptosis of one or more cancer cells in a subject. In certain embodiments, a "therapeutically effective amount" is an amount sufficient to inhibit, reduce the severity of, delay the onset of, suppress, ameliorate, or abrogate one or more symptoms associate with a cancer. In certain embodiments, a "therapeutically effective amount" is an amount sufficient to prolong or sustain life, or improve the quality of life of a subject having a cancer, compared to the length or quality of life that the subject would have in the absence of a cancer treatment. Determination of a therapeutically effective amount is well within the capability of those skilled in the art (e.g., a medical practitioner), especially in light of the detailed disclosure provided herein.

In some embodiments, a therapeutically effective amount is determined by a method described in Huang Jikhan et al., (2004) "Equivalent dose conversion between animals and animals and humans in pharmacological tests", *Clinical Pharmacology and Therapeutics in China,* 9(9): 1069-1072). In some embodiments, a therapeutically effective amount is determined according to certain animal studies described herein. Methods of converting doses from animal experimental models to humans and/or to other mammals is known in the art. In some embodiments, a therapeutically effective amount used for a mouse can be converted to a therapeutically effective amount that can be used for a human according to a body surface area conversion coefficient of 0.0026. In some embodiments, an IFN is administered to a mouse in an amount of $5\times10^4$ to $1\times10^5$ U for a mouse weighing 20 g and, in some embodiments, a quinochalcone compound is administered in an amount of about 5 mg/kg of mouse body weight. Still further, in some embodiments, $1\times10^7$ U to $4\times10^7$ U of an IFN is a therapeutically effective amount that can be administered to a human (e.g., a human having a body weight of about 50-70 kg) based on experiments on mice. In certain embodiments, a therapeutically effective amount of a quinochalcone compound is about 30-50 mg per single dose.

The overall beneficial effect of a treatment described herein can be determined by comparing the condition or disease state of a subject who received a treatment described herein to one or more individuals who have not received treatment, or to the same patient prior to, or after cessation of a treatment. A beneficial effect of a treatment may be complete (no detectable symptoms or cancer) or partial, such that fewer symptoms or amounts of a cancer are observed than would likely occur absent treatment. Accordingly, in some embodiments, a treatment disclosed herein provides for a complete or a partial elimination of a cancer in a subject.

Dose

In certain embodiments, a quinochalcone compound and/or an IFN is administered at a suitable therapeutically effective amount and/or a dose (e.g., at a suitable volume and concentration, which sometimes depends, in part, on a particular route of administration). In some embodiments, a therapeutically effective amount of a quinochalcone compound and/or an IFN is an amount needed to obtain an effective therapeutic outcome. In certain embodiments, a therapeutically effective amount of a quinochalcone compound and/or IFN-β is an amount sufficient to prevent, treat, reduce the severity of, delay the onset of, and/or alleviate a symptom of a neoplastic disorder or cancer, as contemplated herein. In certain embodiments, a therapeutically effective amount of a quinochalcone compound and/or an IFN is an amount sufficient to block, inhibit, ameliorate, abrogate, or suppress growth, viability and/or metastasis of a cancer or cancer cell. In certain embodiments, a therapeutically effective amount of a quinochalcone compound and/or an IFN is an amount sufficient to induce death, necrosis or apoptosis of a cancer or cancer cell. In certain embodiments, a therapeutically effective amount of a quinochalcone compound and/or an IFN is an amount sufficient to decrease, inhibit, or reduce mitosis of a cancer cell.

In certain embodiments, a therapeutically effective amount of a quinochalcone compound and/or an IFN is independently selected from an amount of 0.01 mg/kg (e.g., per kg body-weight of a subject) to 500 mg/kg, 0.1 mg/kg to 500 mg/kg, 0.1 mg/kg to 400 mg/kg, 0.01 mg/kg to 300 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg or 0.1 mg/kg to 1 mg/kg. In certain embodiments a therapeutically effective amount of a quinochalcone compound and/or an IFN is at least 0.01 mg/kg, at least 0.1 mg/kg, at least 1 mg/kg, at least 10 mg/kg, or at least 50 mg/kg. In some aspects a therapeutically effective amount of a quinochalcone compound and/or an IFN is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg. Volumes suitable for various routes of administration are known in the art. For example, 0.1 ml-100 ml of a composition can be safely administered intravenously to an adult human subject.

In certain embodiments, a therapeutically effective amount of IFN comprises a dose in a range of $1\times10^6$ Units (U) to $10\times10^8$ U, $1\times10^6$ U to $1\times10^8$ U, or $1\times10^7$ U to $4\times10^7$U. In certain embodiments, a therapeutically effective amount of IFN comprises a dose in a range of $1\times10^4$ U/ml to $10\times10^8$ U/ml, $1\times10^5$ U/ml to $10\times10^8$ U/ml, $1\times10^6$ U/ml to $10\times10^8$ U/ml, $1\times10^6$ U/ml to $1\times10^8$ U/ml, or $1\times10^6$ U/ml to $1\times10^7$ U/ml.

In some embodiments, composition or preparation comprising a quinochalcone compound and/or an interferon for the treatment of a cancer is a unit preparation. A unit preparation refers to a preparation that meets the requirement of a single administration, such as a unit injection (needle), or a single dose (tablet) or pellet to satisfy a dosage requirement.

In certain embodiments, an amount of a drug required to administer a single administration to a patient can be conveniently obtained by calculating the product of the patient's body weight and the unit body weight required to administer a patient once. In a process of preparation of drugs, an adult weight is generally considered as 50-70 kg. In some embodiments, an initial dose is determined according to an equivalent dose conversion between that used for an experimental animal and a human body weight to determine a dosage. For example, according to the guidance provided by the FDA, SFDA and other drug regulatory agencies, reference may also be made to (Huang Jihan et al., "Equivalent dose conversion between animals and animals and humans in pharmacological tests", "Clinical Pharmacology and Therapeutics in China", 2004 September; 9 (9): 1069-1072), which is incorporated herein by reference. In some embodiments, a dose of human and mouse can be converted according to a body surface area conversion coefficient of 0.0026 of human and mouse.

In some embodiments, HB-48 is administered at a dose of 5 mg/kg of mouse body weight for mice weighing 20 g and IFN-β is administered in an amount of $5 \times 10^4$ to $1 \times 10^5$ U. For example, in some embodiments, HB-48 is formulated as a solution in water or in a pharmaceutical solvent, administered intratumorally or intratumorally to mice at the designed dose, and IFN-β is often administered intratumorally.

In some embodiments, based on experimental dosages administered to mice, which are converted for human administration (e.g., based on a body weight of 50-70 kg), an HB-48 unit preparation drug contains 1-5 mg of HB-48 and $1 \times 10^7$-$4 \times 10^7$ U of IFNβ or IFNγ.

In some embodiments, a pharmaceutical composition containing HB-48 and a conventional pharmaceutical excipient or adjuvant provided by the present disclosure may contain, as an active ingredient, HB-48 in an amount of, for example, of 0.1 to 95% (wt/vol).

In certain embodiments, administering a therapeutically effective amount of a quinochalcone compound and/or an IFN comprises one or more independent administrations. For example, in some embodiments, administering a therapeutically effective amount of a quinochalcone compound and/or an IFN comprises administering a suitable dose daily, every other day, every third day, once weekly, twice weekly, or three times weekly. In some embodiments, administering a therapeutically effective amount of a quinochalcone compound and/or an IFN comprises administering a suitable dose every hour, every 2 hours, every 4 hours, every 6 hours, once a day, twice a day, three times a day, four times a day or more. In some embodiments, administering a therapeutically effective amount of a quinochalcone compound and/ or an IFN comprises administering a constant dose for example, by intravenous administration, over a period of one or more hours, one or more days or one or more weeks. a quinochalcone compound and/or an IFN may be administered at different times, at different doses and at different frequency to obtain an optimal therapeutically effective amount of the combination treatment.

The disclosure has been described herein using specific embodiments for the purposes of illustration only. It will be readily apparent to one of ordinary skill in the art, however, that the principles of the disclosure can be embodied in other ways. Therefore, the disclosure should not be regarded as being limited in scope to the specific embodiments disclosed.

EXAMPLES

Tumor Cells, Drugs and Animals Used in the Following Experiments

Mouse melanoma cell line B16, human breast cancer cell line MCF-7, human melanoma cell line A375, human leukemia cell line K562, human leukemia cell line HL-60 were purchased from US ATCC Center or Peking Union Medical College Foundation Research Center.

MP-1 cells were separated from a clinical melanoma patient tumor sample and were grown in culture with multiple passages.

ALL-1 cells were sterilely obtained from a clinical leukemia patient bone marrow blood and grown under 3D culture conditions.

Female C57BL/C mice, 4-6 weeks and female NOD-SCID mice were purchased from Peking Union Medical College Laboratory Animal Center.

DMF (3',4'-Dimethoxyflavone) was purchased from Sigma (USA).

The quinochalcone derivative HB-48 was synthesized by a method described herein.

Example 1: In 3D Culture Condition, HB-48 can Effectively Inhibit the Growth of Both Solid Tumor and Leukemia Cells Experiment Procedure 3D gel technology was used to culture A375, B16, MP-1, MCF-7, HL-60, K562 and ALL-1 cells at about 3000 cells/well, and the cell status was observed for 2 days. 3D gel technology involves culturing cells in a gel-like matrix. Studies in our lab have shown that cancer cells grown using 3D technology behave more like cancers found in vivo, as cancer cells grown using 3D technology display strong proliferative ability, higher drug resistance, stronger tumorigenicity and greater far-end invasion transfer ability than cancer cells cultured using traditional methods. The following treatments were added to 3D cultures of viable cells.

Control group 1 (Medium): RPMI-1640 medium supplemented with glutamine.

Experiment group1 (HB-48): HB-48 was added to cells at a final concentration of 1 μmol/ml, 5 μmol/ml, 10 μmol/ml, 20 μmol/ml, or 50 μmol/ml in Medium.

Dosing drugs was recorded as day 0. Clone size was determined by taking photographic images 48 and 96 hours after dosing. ImageJ software was used to analyze the size of the clones. The clone sizes in different groups were normalized to the control group on the second day.

Results (FIG. 1A-1G)

As shown in FIG. 1, HB-48 alone significantly inhibited the growth of solid tumor and leukemia cells in a concentration-dependent manner.

Example 2: In 3D Culture Condition, HB-48 Alone can Effectively Reduce the Number of Both Solid Tumor and Leukemia Cells Experiment Procedure 3D gel technology was used to culture A375, B16, MP-1, MCF-7, HL-60, K562 and ALL-1 cells at about 3000 cells/well, and the cell status was observed for 2 days. The following treatments were added to cultures of viable cells.

Control group 1 (Medium): RPMI-1640 medium supplemented with glutamine.

Experiment group1 (HB-48): HB-48 was added to cells at a final concentration of 1 μmol/ml, 5 μmol/ml, 10 μmol/ml, 20 μmol/ml, or 50 μmol/ml in Medium.

The day of drug treatment was recorded as day 0. After 48 and 96 hours, the colonies in 3D soft gel were photographed and the size of colonies were calculated with Image J software. The size of colonies in group control on day 2 is served as control.

Results (FIG. 2A-2G)

Free HB-48 effectively reduced the colony numbers of solid tumor cells and leukemia cells in a dose dependent manner.

Example 3: The Effect of HB-48 Therapy on Solid Tumors was Significantly Better than DMF Therapy Establishment of tumor-bearing mice model: $1\times10^5$ mice melanoma B16 cells were transplanted into 4~6 weeks old C57BL/C mice (C57 mice). The weight of each mouse was about 20 g. Tumors were visible on day 7. Mice were treated as follows when the tumor sizes were 5 mm×5 mm.
- Control group 1 (PBS): Intratumor injection with PBS.
- Experiment group 2 (HB-48): Intratumor injection with HB-48 at 5 mg/kg every two days for 10 days.
- Experiment group 3 (DMF): Intratumor injection with DMF with 5 mg/kg every two days for 10 days.

Tumor sizes were recorded daily.

Results (FIG. 3)

HB-48 and DMF could inhibit the tumor growth and HB-48 shows a significant enhanced anticancer effect.

Example 4: Combination of HB48 and IFNβ Effectively Suppressed the Growth of Solid Tumor Cells and Leukemia Cells Colonies in 3D Culture Experiment Procedure 3D gel technology was used to culture A375, B16, MP-1, MCF-7 cells at about 3000 cells/well. The following treatments were added to cultures of viable cells on day 0.
- Control group 1 (PBS): RPMI-1640 medium supplemented with glutamine (Medium), PBS and drug vehicle DMF.
- Control group 2 (IFN-β): Medium, containing 6 ng/ml murine IFN-β or 10 ng/ml human IFN-β depending on the origin of the cells (e.g., mouse or human).
- Experiment group 3 (HB-48): Medium containing μmol/ml HB-48.
- Experiment group 4 (IFN-β+ DMF): Medium containing 6 ng/ml murine IFN-β or 10 ng/ml human IFN-β and 20 μmol/ml DMF.
- Experiment group 5 (IFN-β+HB-48): Medium containing 6 ng/ml murine IFN-β or 10 ng/ml human IFN-β, and HB-48 (10 μmol/ml).

On days 1, 2, 3, 4 and 5, the colonies in 3D soft gel were photographed and the size of colonies was calculated with Image J software. Results are shown in FIG. 4A-4D.

3D gel technology was used to culture HL-60, K562 and ALL-1 cells at about 3000 cells/well. The following treatments were added to cultures of viable cells on day 0.
- Control group 1 (PBS): RPMI-1640 medium supplemented with glutamine (Medium).
- Experiment group2 (IFN-β+HB-48): Medium containing 6 ng murine IFN-β or 10 ng human IFN-β, and HB-48 at a concentration of 1 μmol/ml, 3 μmol/ml, 5 μmol/ml, 6 μmol/ml, 10 μmol/ml, and 20 μmol/ml.

Dosing drugs was recorded as day 0. Clone size was determined by taking photographic images 48 and 96 hours after dosing. Image J software was used to analyze the size of the clones. The clone sizes in different groups were normalized to the control group. The results are shown in FIGS. 4E, 4F and 4G.

Results (FIG. 4)

The data of FIG. 4 indicated that combination of IFNβ and HB-48 could effectively reduce the colony size of solid tumor cells and leukemia cells with dose-dependence of HB48.

Example 5: Combination of IFN-β and HB-48 Effectively Reduced the Colony Numbers of Solid Tumor Cells and Leukemia Cells Experimental Procedure 3D gel technology was used to culture A375, B16, MP-1, MCF-7, HL-60, K562 and ALL-1 cells at about 3000 cells/well, and the cell status was observed for 2 days. The following treatments were added to cultures of viable cells.
- Control group 1 (PBS): RPMI-1640 medium supplemented with glutamine (Medium).
- Control group 2 (IFN-β): Medium containing 6 ng/ml murine IFN-β or 10 ng/ml human IFNβ.
- Control group 3 (IFNβ+ DMF): Medium containing 6 ng/ml murine IFN-β or 10 ng/ml human IFN-β, and 20 μmol/ml DMF.
- Experiment group 4 (HB-48): Medium containing HB-48 at a concentration of 10 μmol/ml.
- Experiment group 5 (IFNβ+HB-48): Medium containing 6 ng murine IFN-β or 10 ng/ml human IFN-β and HB-48 at a concentration of 10 μmol/ml.

Results (FIG. 5)

FIG. 5 indicated that combination of IFNβ and HB-48 could effectively reduce the colony numbers of solid tumor cells and leukemia cells, which shows enhanced effects compared with IFNβ and DMF combination.

Example 6: Combination of IFNβ and HB-48 could Effectively Induced the Apoptosis of Solid Tumor Cells and Leukemia Cells while Showing No Effects to Cell in Flask Culture Experimental Procedure 3D gel technology was used to culture A375, B16, MP-1, MCF-7, HL-60, K562 and ALL-1 cells at about 8000 cells/well (3D) or at about 30000/well for 6-well plates (Flask), and the cell status was observed for 2 days. The following treatments were added to cultures of viable cells.
- Control group 1 (PBS): RPMI-1640 medium supplemented with glutamine (Medium) and drug solvent.
- Control group 2 (IFN-β): Medium containing 6 ng/ml murine IFN-β or 10 ng/ml human IFNβ.
- Control group 3 (IFNβ+ DMF): Medium containing 6 ng/ml murine IFN-β or 10 ng/ml human IFN-β, and 20 μmol/ml DMF.
- Experiment group 4 (HB-48): Medium containing HB-48 at a concentration of 10 μmol/ml.
- Experiment group 5 (IFNβ+HB-48): Medium containing 6 ng/ml murine IFN-β or 10 ng/ml human IFN-β and HB-48 at a concentration of 10 μmol/ml.

The 3D culture was performed in 24-well plates and the flask culture was performed in 6-well plates. The drugs and culture were homogeneous mixing before added into the plates. Apoptosis was measured 48 hours later. The apoptosis of the cells was determined by FACS.

Results (FIG. 6)

In flask culture (Flask), free IFN-β or IFN-β combined with HB-48 show no obvious cytotoxicity to solid tumor cells and leukemia cells. In 3D culture, IFN-β combined with HB-48 effectively enhanced the cytotoxicity of solid tumor cells and HB-48 in combination showed enhanced effects compared with DMF (FIG. 6).

Example 7: Combination of IFNβ and HB-48 could Inhibit the Solid Tumor Growth and Prolong the Survival Time Combination of IFN-β and HB-48 were used for the treatment of tumor-bearing C57BL/C mice.

Experimental Procedure

Establishment of tumor-bearing mouse model: $1\times10^5$ melanoma B16 cells were transplanted into 4-6 week old C56BL/C mice. Thirty five mice were randomly separated into 5 groups. The weight of each mouse was about 20 grams (g). Tumors were visible on day 7. When the tumor sizes were 5 mm×5 mm, the mice were treated as follows:

Control group 1 (PBS): Intratumor injection with PBS.
Experiment group 2 (IFN-β): Intratumor injection with $1\times10^5$ Units (U) of IFN-β every two days for 10 days.
Experiment group 3 (HB-48): Intratumor injection with HB-48 at 5 mg/kg every two days for 10 days.
Experiment group 4 (IFN-β/HB-48): Intratumor injection with IFN-β ($1\times10^5$ U every two days) and HB-48 (5 mg/kg, every two days). The treatment lasted for 10 days.
Experiment group 5 (IFN-β/DMF): the mice were intratumor injected with IFN-β and DMF (same as experiment 3).

The size of tumors and the date of death was recorded daily.

Figure 7A:
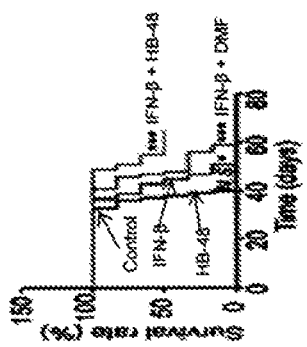
Figure 7B:
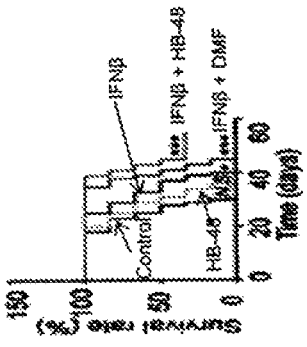

Results (FIG. 7A-7B)

IFN-β combined with DMF or HB-48 significantly inhibited the growth of melanoma (FIG. 7A) and prolonged the survival time of mice (FIG. 7B) compared with control groups.

Figure 7C:
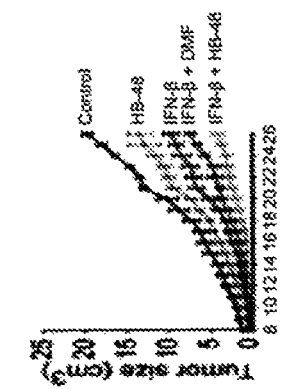
Figure 7D:
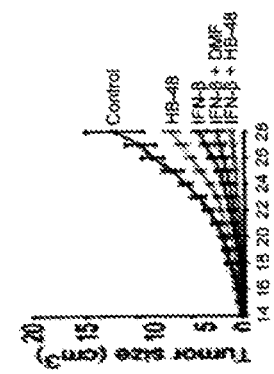

Combination of IFN-β and HB-48 were used for the treatment of tumor-bearing NOD-SCID mice (FIG. 7C-7D).

Experimental Procedure

Establishment of tumor-bearing mouse model: $1\times10^5$ melanoma B16 cells were transplanted into 4-6 week old NOD-SCID mice. Thirty five mice were randomly separated into 5 groups. The weight of each mouse was about 20 grams (g). Tumors were visible on day 7. When the tumor sizes were 5 mm×5 mm, the mice were treated as follows:

Control group 1 (PBS): Intratumor injection with PBS.
Experiment group 2 (IFN-β): Intratumor injection with $1\times10^5$ Units (U) of IFN-β every two days for 10 days.
Experiment group 3 (HB-48): Intratumor injection with HB-48 at 5 mg/kg every two days for 10 days.
Experiment group 4 (IFN-β/HB-48): Intratumor injection with IFN-β ($1\times10^5$ U every two days) and HB-48 (5 mg/kg, every two days). The treatment lasted for 10 days.
Experiment group 5 (IFN-β/DMF): the mice were intratumor injected with IFN-β and DMF (same as experiment 3).

The size of the tumors was measured daily and the death date of the mice was recorded daily.

Results (FIG. 7C-7H)

Combined administration of IFN-β and HB-48 significantly inhibited tumor growth during the administration, both of which were statistically significant (P<0.001) (FIG. 7), and the combination of HB-48 was significantly better than the combination of IFN-β and DMF. Data showed that the combined use of IFN-β and HB-48 significantly prolonged mouse survival (FIGS. 7B and 7H), and the HB-48 combination was significantly better than the IFN-β/DMF combination. In addition, human melanoma cells A375 and human breast cancer cells MCF-7 were also injected subcutaneously into NOD-SCID mice to form tumor-bearing mice. After 10 days, tumor formation was observed and experiments were conducted to find that IFN-β and HB-48 combined showed significant inhibition of tumor growth (see FIG. 7E-7G).

Example 8: HB-48 can Reduce PD-1 Expression in Mouse CD8+ T Cells and Enhance the Killing Function of T Cells The effect of HB-48 on PD-1 expression on activated mouse CD8+ T cells was determined.

Experimental Procedure

Mouse spleen CD8+ T cells were sorted by magnetic beads and seeded in U-bottom 96-well plates (100,000/well) and T cells were activated by anti-CD3/CD28 magnetic beads. The medium was RPMI-1640 plus 10 ng/Mouse IL-2 and 50 nM β-mercaptoethanol. Treatment and dosing is described below:

Control group 1 (PBS): Medium and PBS;
Experimental group 2 (Kyn): Kyn 200 μM was added to the Medium.
Experimental group 3 (Kyn+DMF): Kyn 200 μM and DMF 10 μM were added to the Medium simultaneously.
Experimental group 4 (Kyn+HB-48): Kyn 200 μM and HB-48 10 μM were added to the Medium simultaneously.

PD-1 expression levels were measured by flow cytometry in each group of T cells at 48 hours.

Results

HB-48 inhibited Kyn-mediated upregulation of PD-1 in CD8+ T cells more effectively than DMF, indicating that HB-48 inhibits small molecule receptors more effectively than DMF (FIGS. 8A and 8B).

The effect of HB-48 on the function of specific CD8+ T cells was determined.

Experimental Procedure

Spleen CD8+ T cells of OT-1 mice were obtained by magnetic bead sorting, seeded in a U-shaped bottom 96-well plate (100,000 cells/well) and treated as follows.

Control group 1 (PBS): medium plus PBS.
Experimental group 2 (DMF): DMF 10 μM was added to the medium.
Experimental group 3 (HB-48): HB-48 10 μM was added to the medium.

After pretreatment of T cells for 24 hours, 3D cultured OVA-B16 was co-cultured with OT-1 CD8+ T cells at a ratio of 1 to 10, and the apoptosis of OVA-B16 cells was detected by flow cytometry after 4 hours.

Results

FIG. 8C shows that the percentage of apoptosis of OVA-B16 tumor cells co-cultured with HB-48 pretreated T cells is significantly increased, indicating that HB-48 can significantly inhibit T cell small molecule receptors, down-regulate PD-1 expression and enhance the expression of CD8+ T cell killing function.

Example 9: HB-48 Combined with Specific CD8+ T Cell Adoptive Treatment of Solid Tumors in Mice Significantly Experimental Procedure Tumor-bearing mice were constructed: OVA-B16 melanoma cells were seeded on C57BL/6 mice (inoculation amount of 1×10⁵ cells) for 4-6 weeks. The mice weight was 20 g and tumor formation was observed for 7 days. When the tumor size reached 5 mm×5 mm, tumor-bearing mice were treated as follows:

Control group 1 (PBS): Intratumoral injection of PBS only.

Experimental group 2 (CD8+ T cells): Tumor bearing mice were intravenously adoptively transferred with 4×10⁶ OVA-specific CD8⁺ T-cells (OT-1 T-cells) once every 5 days for 3 times.

Experimental group 3 (DMF): Tumor-bearing mice were intratumorally injected with DMF every two days, a total of 10 times, each dose of 5 mg/kg.

Experimental group 4 (HB-48): Tumor-bearing mice were intratumorally injected with HB-48 every two days, a total of 10 times, each dose of 5 mg/kg.

Experimental group 5 (CD8+ T and DMF): Tumor-bearing mice were intravenously transferred with OT-1 T cells every 5 days for 3 times, and intratumorally injected with DMF every two days for 10 times at the same time.

Experimental group 6 (CD8+ T and HB-48): Tumor-bearing mice were intravenously transfered with OT-1 T cells every 5 days for 3 times, and intratumorally injected with HB-48 every two days for 10 times at the same time.

Tumor length and width were measured daily, and tumor volume changes were calculated.

Results

As can be seen from FIG. 9, adoptive CD8+ T cells alone and HB-48 monotherapy had a certain therapeutic effect. However, CD8+ T cells combined with HB-48 was effective and significantly better than controls. HB-48 could inhibit CD8+ T-cell Aryl hydrocarbon receptor more effectively than DMF and enhance the killing effect of CD8+ T cells in vivo.

Example 10: HB-48 can Reduce PD-1 Expression in Human Peripheral Blood CD8+ T Cells The effect of HB-48 on PD-1 expression in peripheral blood CD8+ T cells of breast cancer patients Experimental Procedure Mononuclear cells were obtained from peripheral blood of breast cancer patients using Ficoll. CD8+ T cells were sorted by magnetic beads and plated on U-bottom 96-well plates (100,000 cells/well) supplemented with RPMI-1640 supplemented with 10 ng/mL human IL-2. Dosing by the following groups:

Control group 1 (PBS): medium plus PBS.

Experimental group 2 (DMF): DMF 10 μM was added to the medium.

Experimental group 3 (HB-48): HB-48 10 μM was added to the medium.

PD-1 expression levels were measured by flow cytometry in each group of T cells at 48 hours.

Results

As can be seen in FIG. 10A and FIG. 10B, HB-48 more effectively down-regulated PD-1 expression in peripheral blood CD8+ T cells in breast cancer patients than did DMF.

The effect of HB-48 on PD-1 expression in peripheral blood CD8+ T cells in patients with active breast cancer was determined.

Experimental Procedure

Mononuclear cells were obtained from peripheral whole blood of patients with breast cancer using Ficoll. CD8+ T cells were sorted by magnetic beads and plated on 96-well U-shaped bottom plates (100,000 cells/well). T cells were activated by anti-CD3/CD28 magnetic beads. Media was RPMI-1640 plus 10 ng/mL human IL-2. Dosing by the following groups:

Control group 1 (PBS): medium and PBS.

Experimental group 2 (Kyn): Kyn 200 μM was added to the medium.

Experimental group 3 (Kyn+DMF): Kyn 200 μM and DMF 10 μM were added to the medium simultaneously.

Experimental group 4 (Kyn+HB-48): Kyn 200 μM and HB-48 10 μM were added to the medium simultaneously.

PD-1 expression levels were measured by flow cytometry in each group of T cells at 48 hours.

Results

As can be seen in FIG. 10C and FIG. 10D, HB-48 inhibited Kyn-mediated upregulation of PD-1 in peripheral blood CD8+ T cells in patients with breast cancer more effectively than DMF, indicating that HB-48 inhibits human CD8+T more effectively than DMF on Small cell receptor.

The effect of HB-48 on the expression of Kyn transporter PAT4 in activated human peripheral blood CD8+ T cells was determined.

Experimental Procedure

Mononuclear cells were obtained from peripheral whole blood of patients with breast cancer using Ficoll. CD8+ T cells were sorted by magnetic beads and plated on 96-well U-shaped bottom plates (100,000 cells/well). T cells were activated by anti-CD3/CD28 magnetic beads. Media was RPMI-1640 plus 10 ng/mL human IL-2. Dosing by the following groups:

Control group 1 (PBS): medium and PBS.

Experimental group 2 (Kyn): Kyn 200 μM was added to the medium.

Experimental group 3 (Kyn+DMF): Kyn 200 μM and DMF 10 μM were added to the medium simultaneously.

Experimental group 4 (Kyn+HB-48): Kyn 200 μM and HB-48 10 μM were added to the medium simultaneously.

Each group of T cells RNA was extracted after 48 hours, and the expression of PAT4 was detected by fluorescence quantitative PCR.

Results

FIG. 10E shows that Kyn can up-regulate the expression of its transporter PAT4, while HB-48 can down-regulate the expression of PAT4 in peripheral blood CD8+ T cells in breast cancer patients more effectively than DMF. The results showed that HB-48 could inhibit the uptake of Kyn by CD8+ T cells and decrease the expression of PD-1.

Taken together, the results of the Examples above showed that HB-48 used alone or in combination with IFN-β can effectively kill the solid tumor (e.g., A375, B16, MP-1 and MCF-7) and leukemia cells (e.g., HL-60, K562 and ALL-1), enhanced the killing effect, and inhibited tumor growth. The results also showed that compared with DMF, HB-48 significantly reduced PD-1 expression on CD8+ T cells, inhibited Kyn-mediated up-regulation of PD-1 and enhanced the cytotoxicity of specific CD8+ T cells to various tumor cells.

Example 11

Studies of small molecule inhibitors HB-48 and IFNβ or IFNγ on solid tumors and leukemia. This experiment shows that HB-48 in combination with IFNβ or IFNγ effectively inhibits the growth of solid tumor and leukemia cell clones in 3D culture conditions.

Experiment Procedure

A375, B16, MP-1, MCF-7, HL-60, K562 and ALL-1 were seeded into a 3D soft gel (3000/well) and the cellular morphology was observed after 2 days. The cultured cells are divided into a control group and an experimental group, which is treated as follows:

Control 1 (control): medium supplemented with glutamine (e.g., RPMI-1640 medium);

Control group 2 (IFNβ or IFNγ): 6 ng/ml murine or 10 ng/ml human IFNβ/IFNγ in glutamine supplemented medium (e.g., RPMI-1640 medium);

Control group 3 (IFNβ/IFNγ+ DMF): 6 ng/ml murine or 10 ng/mg human IFNβ/IFNγ and 20 μmol/ml DMF were added to medium supplemented with glutamine (RPMI-1640 medium, for example);

Experimental group 4 (HB-48): 10 μmol/ml HB-48 was added to medium supplemented with glutamine (e.g., RPMI-1640 medium);

Experimental group 5 (IFNβ/IFNγ+ HB-48): 6 ng/ml murine or 10 ng/ml human IFNβ/IFNγ and 10 μmol/ml HB-48 were added to glutamine supplemented medium (e.g., RPMI-1640 medium);

Experimental group 6 (IFNβ/IFNγ+ HB-48): 6 ng/ml murine or 10 ng/ml human IFNβ/IFNγ and different concentrations of HB-48 were added to glutamine supplemented medium (e.g., RPMI-1640 medium).

Drugs were mixed evenly in medium and then added to each group of experimental groups. The day of drug treatment was recorded as the day 0. The cells were photographed in 48 and 96 hours. Image J software was used to analyze the size of the clones. The relative size of the clones in different groups at different time points was calculated based on the cloned size of the control group on the second day, and the statistical analysis was performed.

Note: The experiment uses "mouse IFNβ/IFNγ" or "human IFNβ/IFNγ" according to the properties of the cultured tumor cells, and the following examples are the same.

Results

The relative cloning sizes results of each group and different concentrations of HB-48 effects on the size of cell clones in IFNβ/IFNγ+ HB-48 experimental group are shown in FIG. 11A-FIG. 11H is the results of three control groups and experimental groups 4. FIG. 11I-FIG. 11N is the result of experimental group 6.

In FIG. 11, the small molecule inhibitors DMF and HB-48 combined with IFNβ/IFNγ showed better tumor inhibition effect. But the experimental group IFNβ/IFNγ and HB-48 (IFNβ/IFNγ+ HB-48) showed enhanced inhibition in solid tumor and leukemia cell clone size. The HB-48 is concentration-dependent and statistical results were significantly different.

Example 12

HB-48 combined with IFNβ/IFNγ are effective to reduce the clone number of solid tumors and leukemia cells under 3D culture conditions.

Experiment Procedure

Using 3D gel technology to culture A375, B16, MP-1, MCF-7, HL-60, K562 and ALL-1 cells at about 3000 cells/well, and the cell status was observed after 2 days. Under the good status of cells, adding drugs as following list:

Group control 1 (control): common culture medium with Glutamine (such as RPMI 1640 culture medium);

Experiment group 2 (IFNβ/IFNγ): adding 6 ng/ml murine or 10 ng/ml human IFNβ/IFNγ to common culture medium with Glutamine (such as RPMI 1640 culture medium);

Experiment group 3 (IFNβ/IFNγ+DMF): adding 6 ng/ml murine or 10 ng/ml human IFNβ/IFNγ plus with 20 μmol/ml DMF to common culture medium with Glutamine (such as RPMI 1640 culture medium);

Experiment group 4 (HB48): small molecule inhibitor HB-48 was added to normal glutamine supplemented medium (such as RPMI-1640 medium);

Experiment group 5 (IFNβ/IFNγ+HB-48): adding 6 ng/ml murine or 10 ng/ml human IFNβ/IFNγ plus with 10 μmol/ml HB-48 to common culture medium with Glutamine (such as RPMI 1640 culture medium).

Medium and drugs need to be mixed evenly before adding to each group. Dosing start recorded as day 0, the number of clone numbers were counted on the fourth day under microscope, Results The results of the clone numbers in each group were shown in FIG. 12. The corresponding statistical results are shown in FIG. 12, from left to right in the histogram for each tumor cell, which in turn represents the control group, the IFNβ group, the IFNβ/IFNγ+DMF groups, the HB-48 group and the IFNβ/IFNγ+HB-48 groups.

As shown in FIG. 12, the experimental group treated with HB-48 combining IFNβ/IFNγ can effectively reduce the clone numbers of solid tumor and leukemia cells, and the effect was significantly better than IFNβ/IFNγ combined with DMF.

Example 13

The effect of HB-48 on the expression of macrophage inflammatory factors derived from mouse bone marrow. HB-48 significantly inhibits the expression of inflammatory factors secreted by macrophages derived from murine bone marrow.

Experiment Procedure

Bone marrow-derived macrophages were obtained from mouse bone marrow cells, RPMI-1640 plus mouse M-CSF 20 ng/mL for 5 days and were treated as follows:

Control group 1 (PBS): medium plus PBS;

Experimental group 2 (HB-48): medium plus HB-48 at a dose of 10 μM.

After 48 h, macrophages were collected and the expression of IFN-γ, TNF-α, IL-12p35, IL-12p40 and IL-2 was detected by qPCR in both groups.

Results

As shown in FIG. 13, the expressions of IFN-γ, TNF-α, IL-12p35, IL-12p40 and IL-1β were significantly reduced in the HB-48 treated group, indicating that HB-48 could remarkably inhibit inflammatory factors secreted from macrophages.

The above data is representative of a large number of studies. In summary, the Examples of Example 1 to Example 13, show that the small molecule inhibitor HB-48 can effectively inhibit the malignant growth of solid tumors and leukemias. Further, when the small molecule inhibitors HB-48 and IFNβ or IFNγ were used in combination, a better therapeutic effect was observed with a reduced dose of a single drug, indicating that the small molecule inhibitor HB-48 combined with IFNβ can not only reduce the dosage for effective treatment, but can also significantly enhance the efficacy. Enhanced anticancer effects and suppression of tumor growth could be obtained in clinical treatment. Compared with DMF, HB-48 (a small molecule inhibitor) can significantly reduce PD-1 expression in CD8+ T cells, inhibit Kyn-mediated upregulation of PD-1, and enhance specific CD8+ T cell cytotoxicity to tumor cells.

Example 14

Embodiments

A1. A composition comprising a quinochalcone compound, or a salt thereof, wherein the quinochalcone compound comprises the structure of formula I:

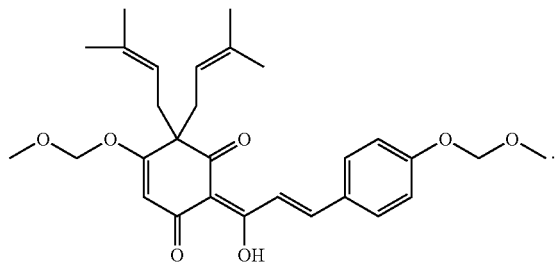

(I)

A2. The composition of embodiment A1, further comprising an Interferon (IFN), or a variant thereof.
A2.1. The composition of any one of embodiments A1 to A2, further comprising an organic solvent.
A2.2. The composition of A2.1, wherein the organic solvent is 3',4'-Dimethoxyflavone (DMF).
A2.3. The composition of any one of embodiments A1 to A2.2, wherein the composition induces apoptosis, necrosis, autophagy, or death, of a cancer, a cancer cell, a malignant cell, a tumor cell, a differentiated tumor cell, a tumor stem cell or a dormant tumor stem cell.
A2.4. The composition of any one of embodiments A1 to A2.3, wherein the composition inhibits, suppresses, abrogates or terminates growth, viability or metastasis of a cancer, a cancer cell, a malignant cell, a tumor cell, a differentiated tumor cell, a tumor stem cell or a dormant tumor stem cell.
A3. The composition of any one of embodiments A2 to A2.4, wherein the IFN is IFN-β, or a biologically active variant thereof.
A3.1. The composition of embodiment A2.5, wherein the IFN-β is human IFN-β.
A4. The composition of any one of embodiments A2 to A2.4, wherein the IFN is IFN-γ, or a biologically active variant thereof.
A4.1. The composition of embodiment A4, wherein the IFN-γ is human IFN-γ.
A5. The composition of any one of embodiments A1 to A4.1, wherein the compositions is a pharmaceutical composition comprising one or more pharmaceutically acceptable excipients.
A6. The composition of any one of embodiments A1 to A5, wherein the composition comprises an amount of the quinochalcone compound in a range of 1 µg to 100 g, 1 mg to 100 g, 100 mg to 10 g, or 1 g to 10 g.
A7. The composition of any one of embodiments A1 to A6, wherein the composition comprises an amount of the quinochalcone compound in a range of 1 ng/ml to 1 g/ml, 1 µg/ml to 100 mg/ml, or 100 ug/ml to 100 mg/ml.
A8. The composition of any one of embodiments A2 to A7, wherein the composition comprises an amount of the IFN in a range of $1\times10^6$ Units (U) to $10\times10^8$ U, $1\times10^6$ U to $1\times10^8$ U, or $1\times10^7$ U to $4\times10^7$ U.
A9. The composition of any one of embodiments A2 to A8, wherein the composition comprises an amount of the IFN in a range of $1\times10^4$ U/ml to $10\times10^8$ U/ml, $1\times10^5$ U/ml to $10\times10^8$ U/ml, $1\times10^6$ U/ml to $10\times10^8$ U/ml, $1\times10^6$ U/ml to $1\times10^8$ U/ml, or $1\times10^6$ U/ml to $1\times10^7$ U/ml.
B1. A method of treating a cancer in a subject in need thereof comprising administering to the subject a therapeutically effective amount of the composition of any one of embodiments A1 to A9.
B2. The composition of any one of embodiments A1 to A9, for use in treating a cancer in a subject, wherein the subject has or is suspected of having a cancer.
B3. The composition for use of embodiment B2, wherein the subject is a human.
C1. A method of treating a cancer in a subject in need thereof comprising administering to the subject a therapeutically effective amount of a quinochalcone compound, or a salt thereof, and a therapeutically effective amount of an IFN, or a biologically active variant thereof.
C1.1. The method of embodiment C1, wherein the quinochalcone compound comprises the structure of formula I:

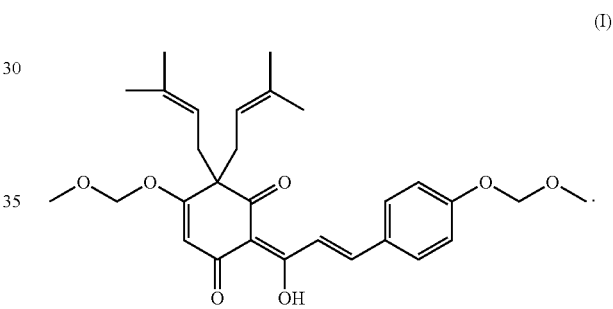

(I)

C2. The method of any one of embodiments C1 to C1.1, wherein the IFN is IFN-β, or a biologically active variant thereof, or wherein the IFN is IFN-γ, or a biologically active variant thereof.
C2.1. The method of any one of embodiments C1 to C2, wherein the IFN is a human IFN, or a biologically active variant thereof.
C3. The method of any one of embodiments B1, and C1 to C2, wherein the subject is a human.
C4. The method of any one of embodiments B1 to B3, and C1 to C3, wherein the subject has or is suspected of having a cancer.
C5. The method of any one of embodiments B1 to B3, and C1 to C4, wherein the cancer is a neoplasm or tumor.
C6. The method of any one of embodiments B1 to B3, and C1 to C5, wherein the cancer is a malignant and/or a metastatic cancer.
C7. The method of any one of embodiments B1 to B3, and C1 to C5, wherein the cancer is or non-metastatic.
C8. The method of any one of embodiments B1 to B3, and C1 to C7, wherein the cancer is selected from the group consisting of a carcinoma, a sarcoma, a neuro neoplasia, a lymphoma, a myeloma, a leukemia, a melanoma, a mesothelioma, a solid or soft tissue tumor, and a secondary cancer.
C9. The method of embodiment C8, wherein the carcinoma is selected from a respiratory system carcinomas, gastrointestinal system carcinomas, genitourinary system carcinomas, testicular carcinomas, prostatic carcinomas, endocrine system carcinomas, basal cell carcinoma of the skin, carcinoma of unknown primary, cholangiocarcinoma, ductal carcinoma in situ (DCIS), merkel cell carcinoma, lung carcinoma, thymoma and thymic carcinoma, midline tract carcinoma, lung small cell carcinoma, thyroid carcinoma, liver hepatocellular carcinoma, squamous cell carcinoma, head and neck squamous carcinoma, breast carcinoma, epithelial carcinoma, adrenocortical carcinoma, ovarian surface epithelial carcinoma, and the like.

C10. The method of embodiment C8, wherein the carcinoma is selected from a carcinoma of the uterus, cervix, colon, pancreas, kidney, esophagus, stomach and ovary.

C11. The method of embodiment C8, wherein the sarcoma is selected from the group consisting of an Ewing sarcoma, lymphosarcoma, liposarcoma, osteosarcoma, soft tissue sarcoma, Kaposi sarcoma, rhabdomyosarcoma, uterine sarcoma, chondrosarcoma, leiomyosarcoma, fibrosarcoma and the like.

C12. The method of embodiment C8, wherein the neuro neoplasia is selected from the group consisting of a glioma, glioblastoma, meningioma, neuroblastoma, retinoblastoma, astrocytoma, oligodendrocytoma, and the like.

C13. The method of embodiment C8, wherein the lymphoma, myeloma or leukemia is selected from the group consisting of myeloblastic leukemia, multiple myeloma, poorly differentiated acute leukemias (e.g., erythroblastic leukemia and acute megakaryoblastic leukemia), acute promyeloid leukemia (APML), acute myelogenous leukemia (AML), chronic myelogenous leukemia (CML), acute lymphoblastic leukemia (ALL), which includes B-lineage ALL and T-lineage ALL, chronic lymphoblastic leukemia, chronic lymphocytic leukemia (CLL), prolymphocytic leukemia (PLL), hairy cell leukemia (HLL), Waldenstrom's macroglobulinemia (WM), non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease, Reed-Sternberg disease, and variants thereof.

C14. The method of embodiment C8, wherein the soft or solid tissue tumor is selected from visceral tumors, seminomas, hepatomas, and other solid or soft tumors of the breast, liver, lung, pancreas, uterus, ovary, testicle, head, neck, eye, brain, mouth, pharynx, vocal cord, ear, nose, esophagus, stomach, intestine, colon, adrenal, kidney, bone, bladder, urethra, carcinomas, lung, muscle, skin, feet, hands, and soft tissue.

C15. The method of any one of embodiments B1 to B3, and C1 to C14, further comprising administering an anti-cancer treatment to the subject.

C16. The method of embodiment C15, wherein the anti-cancer treatment comprises administering an anti-cancer vaccine to the subject.

C17. The method of embodiment C15, wherein the anti-cancer treatment comprises administering a chemotherapeutic agent or radiation therapy to the subject.

C18. The method of embodiment C15, wherein the anti-cancer treatment comprises administering an immunotherapy to the subject.

C19. The method of embodiment C18, wherein the immunotherapy comprises administering an antibody that specifically binds to CD20, CD52, CD274, CD279, CTLA-4, Programmed Death Ligand 1 (PD-L1), Programmed cell death-1 (PD-1), or PD-1 receptor.

C20. The method of any one of embodiments B1 to B3, and C1 to C19, wherein the quinochalcone compound and the IFN are administered to the subject at the same time.

C21. The method of any one of embodiments B1 to B3, and C1 to C19, wherein the quinochalcone compound and the IFN are administered to the subject at different times.

C22. The method of embodiment C21, wherein the quinochalcone compound and the IFN are administered to the subject within 5 minutes, within 1 to 12 hours, or within 1 to 2 days of each other.

C23. The method of any one of embodiments B1 to B3, and C1 to C22, wherein the therapeutically effective amount of the quinochalcone compound comprises an amount in a range of 1 µg/kg (wt. of API/body weight of subject) to 10 g/kg, 1 mg/kg to 10 g/kg, 1 mg/kg to 1 g/kg, 1 mg/kg to 100 mg/kg, or 1 mg/kg to 10 mg/kg.

C24. The method of embodiment C23, wherein the therapeutically effective amount of the quinochalcone compound is administered at a frequency selected from once a month, once a week, twice a week, three times a week, four times a week, five times a week, once a day, twice a day, three time a day, four times a day, five times a day, intervening intervals thereof, or a combination thereof.

C25. The method of any one of embodiments B1 to B3, and C1 to C24, wherein the therapeutically effective amount of the IFN is an amount in a range of 1 ug to 1000 ug, 10 ug to 500 ug, 25 ug to 300 ug or 30 ug to 250 ug administered at a frequency selected from once a month, twice a month, once a week, twice a week, every other day or daily.

D1. A quinochalcone compound, or salt thereof, comprising the structure of formula I:

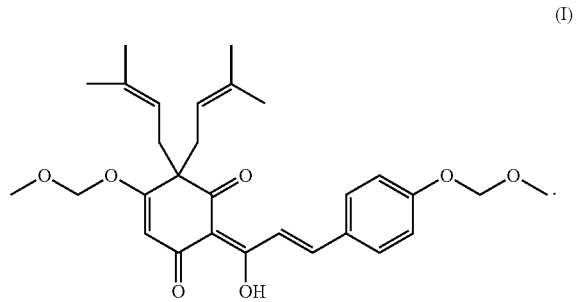

(I)

D2. The quinochalcone compound of embodiment D1, wherein the quinochalcone compound is HB-48.

D3. A method of inducing apoptosis, necrosis, autophagy, or death, of a cancer, a cancer cell, a malignant cell, a tumor cell, a differentiated tumor cell, a tumor stem cell or a dormant tumor stem cell comprising contacting the cancer, the cancer cell, the malignant cell, the tumor cell, the differentiated tumor cell, the tumor stem cell or the dormant tumor stem cell with the quinochalcone compound of embodiment D1 or D2.

D4. The method of embodiment D3, further comprising contacting the cancer, the cancer cell, the malignant cell, the tumor cell, the differentiated tumor cell, the tumor stem cell or the dormant tumor stem cell with IFNβ or IFNγ.

D5. The quinochalcone compound of embodiment D1 or D2 for use in suppressing, abrogating or terminating growth, viability or metastasis of a cancer, a cancer cell, a malignant cell, a tumor cell, a differentiated tumor cell, a tumor stem cell or a dormant tumor stem cell.

D6. A composition comprising (i) the quinochalcone compound of embodiment D1 or D2 and (ii) IFNβ or IFNγ for use in suppressing, abrogating or terminating growth, viability or metastasis of a cancer, a cancer cell, a malignant cell, a tumor cell, a differentiated tumor cell, a tumor stem cell or a dormant tumor stem cell.

E1. A method of inducing apoptosis, necrosis, autophagy, or death, of a cancer, a cancer cell, a malignant cell, a tumor cell, a differentiated tumor cell, a tumor stem cell or a dormant tumor stem cell comprising contacting the cancer, the cancer cell, the malignant cell, the tumor cell, the differentiated tumor cell, the tumor stem cell or the dormant tumor stem cell with the composition of any one of embodiments A1 to A9.

E2. The method of embodiment E1, wherein the contacting induces apoptosis, necrosis, autophagy, or death, of the cancer, the cancer cell, the malignant cell, the tumor cell, the differentiated tumor cell, the tumor stem cell or the dormant tumor stem cell.

E3. The method of embodiment E2, wherein the contacting induces apoptosis, necrosis, autophagy, or death, of the differentiated tumor cell and the dormant tumor stem cell.

E4. A method of inhibiting, suppressing, abrogating or terminating growth, viability or metastasis of a cancer, a cancer cell, a malignant cell, a tumor cell, a differentiated tumor cell, a tumor stem cell or a dormant tumor stem cell comprising contacting the cancer, the cancer cell, the malignant cell, the tumor cell, the differentiated tumor cell, the tumor stem cell or the dormant tumor stem cell with the composition of any one of embodiments A1 to A9.

E5. The method of embodiment E4, wherein the contacting inhibits, suppresses, abrogates or terminates growth, viability or metastasis of the cancer, the cancer cell, the malignant cell, the tumor cell, the differentiated tumor cell, the tumor stem cell or the dormant tumor stem cell.

E6. The method of embodiment E5, wherein the contacting inhibits, suppresses, abrogates or terminates growth, viability or metastasis of the differentiated tumor cell and the dormant tumor stem cell.

F1. A method of inhibiting, reducing, suppressing, abrogating, or blocking PD-1 expression on a CD8+ T-cell comprising contacting a CD8+ T-cell with the composition of any one of embodiments A1 to A9 thereby inhibiting, reducing, suppressing, abrogating, or blocking PD-1 expression on the CD8+ T-cell.

F2. The method of F1, wherein the PD-1 expression on the CD8+ T-cell is a results of Kyn-mediated upregulation of the PD-1.

F3. A method of inhibiting, reducing, suppressing, abrogating, or blocking kyn-mediated expression of PD-1 on a CD8+ T-cell comprising (i) providing a CD8+ T-cell that was previously contacted with kyn, and (ii) contacting the CD8+ T-cell with the composition of any one of embodiments A1 to A9, thereby inhibiting, reducing, suppressing, abrogating, or blocking PD-1 expression on the CD8+ T-cell.

G1. A method of inducing or enhancing tumor cell cytotoxicity mediated by a CD8+ T-cell comprising: (i) contacting a CD8+ T-cell with the composition of any one of embodiments A1 to A9 and (ii) contacting the CD8+ T-cell with a tumor cell thereby inducing or enhancing cytotoxicity of the tumor cell by the CD8+ T-cell.

H1. The composition of any one of embodiments A1 to A9, or the quinochalcone compound of any one of embodiments D1 to D4 for use in the treatment of inflammation.

H2. The composition of embodiment H1, wherein the inflammation is vasculitis, arthritis, osteoarthritis, or colitis.

J1. An edible food for human consumption comprising a composition of any one of embodiments A1 to A9, or the quinochalcone compound of any one of embodiments D1 to D4.

K1. A method of treating inflammation in a subject in need thereof comprising administering to the subject a therapeutically effective amount of the composition of any one of embodiments A1 to A9, or the quinochalcone compound of any one of embodiments D1 to D4.

L1. A composition comprising HB-48.

L2. The composition of embodiment L1 further comprising IFN-β, or a variant thereof.

L3. The composition of embodiment L1 or L2, wherein the compositions is a pharmaceutical composition comprising one or more pharmaceutically acceptable excipients.

L4. The composition of embodiment L2 or L3, wherein the IFN-β is human IFN-β.

L5. The composition of any one of embodiments L2 to L4, wherein the variant of IFN-β is a biologically active variant.

L6. A method of treating a cancer in a subject in need thereof comprising administering to the subject a therapeutically effective amount of the composition of any one of embodiments L1 to L5.

L7. A method of treating a cancer in a subject in need thereof comprising administering to the subject a therapeutically effective amount of HB-48, alone or in combination with a therapeutically effective amount of IFN-β.

L8. The method of embodiment L6 or L7, wherein the IFN-β is human IFN-β, or a biologically active variant thereof.

L9. The method of any one of embodiments L6 to L8, wherein the subject is a human.

L10. The method of any one of embodiments L6 to L9, wherein the cancer is selected from a lymphoma, leukemia, hematopoietic neoplasia, myeloma, melanoma and solid tumor.

L11. The method of any one of embodiments L6 to L11, further comprising administering an anti-cancer treatment to the subject.

L12. The method of embodiment L11, wherein the anti-cancer treatment comprises administering an anti-cancer vaccine to the subject.

L13. The method of embodiment L11, wherein the anti-cancer treatment comprises administering a chemotherapeutic agent to the subject.

L14. The method of any one of embodiments L6 to L13, wherein the HB-48 and the IFN-β are administered to the subject at the same time.

L15. The method of any one of embodiments L6 to L13, wherein the HB-48 and the IFN-β are administered to the subject at different times.

L16. The method of embodiment L15, wherein the HB-48 and the IFN-β are administered within 5 minutes, within 1 to 12 hours, or within 1 to 2 days of each other.

M1. A quinone chalcone (quinochalcone) compound for preparing a medicament for treating tumor diseases, wherein the quinone chalcone compound has the following structure:

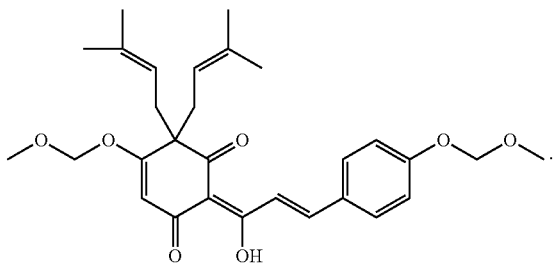

M2. The use according to embodiment M1, wherein the oncological diseases include breast cancer, malignant melanoma, lung cancer, liver cancer, pancreatic cancer, brain tumor or leukemia.

M3. The use according to embodiment M1 or M2, wherein the drug for treating oncological diseases includes injection and oral dosage forms.

M4. The use according to any one of embodiments M1 to M3, wherein the agent for treating tumor diseases is a unit preparation.

M5. The use according to embodiment M4, wherein 1-5 mg of said quinone chalcone compound as an active ingredient is contained in a medicine of said unit preparation.

M6. The use according to any one of embodiments M1 to M3, wherein the agent for treating tumor diseases is a combination of agents comprising a therapeutically effective amount of interferon and the quinone chalcone compound.

M7. The use according to embodiment M6, wherein the agent for treating tumor diseases is a unit preparation.

M8. The use according to embodiment M7, wherein the drug of the unit dosage form comprises a tumor-therapeutically effective amount of interferon and 1-5 mg of the quinone chalcone compound as an active ingredient.

M9. The use according to embodiment M8, wherein the unit preparation contains $1 \times 10^7$ to $4 \times 10^7$ U interferon in the drug.

M10. The use according to any one of embodiments M1 to M4, wherein the drug for treating tumor diseases is a combination of a preparation comprising a clinical anti-tumor drug and the quinone chalcone compound.

M11. The use according to embodiment M10, wherein the clinical anti-tumor drug comprises an anti-tumor vaccine or a chemotherapeutic drug.

M12. A combination of agents for preparation of antineoplastic agents, wherein the therapeutically active ingredient comprises an interferon and the quinone chalcone compound according to embodiment M1.

M13. The preparation combination according to embodiment M12, wherein the preparation combination is a unit preparation.

M14. The combination of embodiment M13, wherein the unit dosage formulation comprises a therapeutically effective amount of a tumor interferon and 1-5 mg of the quinone chalcone compound as an active ingredient.

M15. The preparation according to embodiment M14, wherein the unit preparation comprises $1 \times 10^7$ to $4 \times 10^7$ U of interferon.

M16. The combination of agents according to embodiments M12-M15, said interferon being selected from interferon beta or interferon gamma.

M17. A combination of antineoplastic agents, wherein the therapeutically active ingredients comprise the quinone chalcone compound of embodiment M1 and a clinical antineoplastic agent.

M18. The combination of embodiment M17, wherein the clinical anti-tumor drug comprises an anti-tumor vaccine or a chemotherapeutic agent.

The entirety of each patent, patent application, publication or any other reference or document cited herein hereby is incorporated herein by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described herein.

All of the features described herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an amount that is "less than" includes any non-zero amount less than a recited reference number.

Reference to a series of ranges includes ranges which combine the values of the boundaries of different ranges within the series. Thus, to illustrate reference to a series of ranges, for example, of 1-10 and 10-20, includes ranges of 1-20.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The disclosure is generally described herein using affirmative language to describe the numerous embodiments and aspects. The disclosure also specifically includes embodiments in which particular subject matter is excluded, in full or in part, such as substances or materials, method steps and conditions, protocols, or procedures. For example, in certain embodiments or aspects of the disclosure, materials and/or method steps are excluded. Thus, even though the disclosure is generally not expressed herein in terms of what the disclosure does not include aspects that are not expressly excluded in the disclosure are nevertheless described herein.

The technology illustratively described herein suitably can be practiced in the absence of any element(s) not specifically described herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 80%, at least 85%, at least 90%, at least 95%", "at least 96%", "at least 97%","at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

The term "specifically binds" refers to a binding agent binding to a target protein or peptide in preference to binding other molecules or other peptides in a particular assay in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

What is claimed is:

1. A composition comprising a quinochalcone compound, or a salt thereof, wherein the quinochalcone compound is shown by formula I:

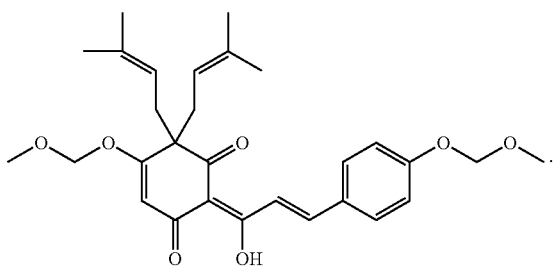

2. The composition of claim 1 further comprising an interferon, or a variant thereof, wherein the interferon is IFN-β or IFN-γ.

3. The composition of claim 1, wherein the composition is a pharmaceutical composition comprising one or more pharmaceutically acceptable additives or excipients.

4. The composition of claim 2, wherein the interferon is a human interferon.

5. The composition of claim 2, wherein the variant of the interferon is a biologically active variant.

6. A method of treating a cancer, or inflammation or an inflammatory condition in a subject in need thereof comprising administering to the subject a therapeutically effective amount of the composition of claim 1.

7. A method of treating a cancer, or inflammation or an inflammatory condition in a subject in need thereof comprising administering to the subject a therapeutically effective amount of a quinochalcone compound, or a salt thereof, wherein the quinochalcone compound is shown by formula I:

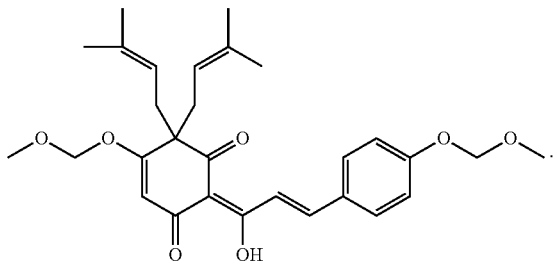

8. The method of claim 7, further comprising administering to the subject a therapeutically effective amount of a IFN-β or IFN-γ.

9. The method of claim 8, wherein the IFN-β or IFN-γ is a human interferon, or a biologically active variant thereof.

10. The method of claim 6, wherein the subject is a human.

11. The method of claim 7, wherein the subject is a human.

12. The method of claim 6, wherein the cancer is selected from a lymphoma, leukemia, hematopoietic neoplasia, myeloma, melanoma and solid tumor, the inflammation or inflammatory condition comprises an autoimmune disorder or pro-inflammatory condition selected from the group consisting of polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatic, Spondyloarthritides, Pulmonary arterial hypertension, graft-versus-host disease, autoimmune myocarditis, contact hypersensitivity (contact dermatitis), gastro-esophageal reflux disease, erythroderma, Behcet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility, immune-mediated infertility, headache, migraine, pain and swelling.

13. The method of claim 7, wherein the cancer is selected from a lymphoma, leukemia, hematopoietic neoplasia, myeloma, melanoma and solid tumor, the inflammation or inflammatory condition comprises an autoimmune disorder or pro-inflammatory condition selected from the group consisting of polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatic, Spondyloarthritides, Pulmonary arterial hypertension, graft-versus-host disease, autoimmune myocarditis, contact hypersensitivity (contact dermatitis), gastro-esophageal reflux disease, erythroderma, Behcet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility, immune-mediated infertility, headache, migraine, pain and swelling.

14. The method of claim 6, further comprising administering an anti-cancer treatment to the subject.

15. The method of claim 7, further comprising administering an anti-cancer treatment to the subject.

16. The method of claim 14, wherein the anti-cancer treatment comprises administering an anti-cancer vaccine or chemotherapeutic agent to the subject.

17. The method of claim 15, wherein the anti-cancer treatment comprises administering an anti-cancer vaccine or chemotherapeutic agent to the subject.

18. The method of claim 8, wherein the quinochalcone compound, or a salt thereof, and the IFN-β or IFN-γ are administered to the subject at the same time or at different times.

19. The method of claim 18, wherein the quinochalcone compound, or a salt thereof, and the IFN-β or IFN-γ are administered within 5 minutes, within 1 to 12 hours, or within 1 to 2 days of each other.

* * * * *